United States Patent
Wang et al.

(10) Patent No.: US 10,570,141 B2
(45) Date of Patent: Feb. 25, 2020

(54) SUBSTITUTED PYRROLOPYRIMIDINE CDK INHIBITOR, PHARMACEUTICAL COMPOSITION CONTAINING SAME AND USE THEREOF

(71) Applicants: CHIA TAI TIANQING PHARMACEUTICAL GROUP CO., LTD., Lianyungang (CN); CENTAURUS BIOPHARMA CO., LTD., Beijing (CN); LIANYUNGANG RUNZHONG PHARMACEUTICAL CO., LTD., Lianyungang (CN)

(72) Inventors: Shulong Wang, Beijing (CN); Kuncheng Chen, Beijing (CN); Xijie Liu, Beijing (CN); Yuandong Hu, Beijing (CN); Bo Liu, Beijing (CN); Yong Peng, Beijing (CN); Hong Luo, Beijing (CN); Yongxin Han, Beijing (CN); Shanchun Wang, Lianyungang (CN); Mei Liu, Lianyungang (CN); Hongjiang Xu, Lianyungang (CN)

(73) Assignees: CHIA TAI TIANQING PHARMACEUTICAL GROUP CO., LTD., Jiangsu (CN); CENTAURUS BIOPHARMA CO., LTD., Beijing (CN); LIANYUNGANG RUNZHONG PHARMACEUTICAL CO., LTD., Jiangsu (CN)

( * ) Notice: Subject to any disclaimer, the term of this patent is extended or adjusted under 35 U.S.C. 154(b) by 0 days.

(21) Appl. No.: 16/087,918

(22) PCT Filed: Mar. 27, 2017

(86) PCT No.: PCT/CN2017/078260
§ 371 (c)(1),
(2) Date: Sep. 24, 2018

(87) PCT Pub. No.: WO2017/162215
PCT Pub. Date: Sep. 28, 2017

(65) Prior Publication Data
US 2019/0300533 A1 Oct. 3, 2019

(30) Foreign Application Priority Data
Mar. 25, 2016 (CN) .......................... 2016 1 0180458

(51) Int. Cl.
*C07D 487/04* (2006.01)
*A61K 31/519* (2006.01)
*A61P 35/00* (2006.01)

(52) U.S. Cl.
CPC .......... *C07D 487/04* (2013.01); *A61K 31/519* (2013.01); *A61P 35/00* (2018.01)

(58) Field of Classification Search
CPC ...... C07D 487/04; A61K 31/519; A61P 35/00
USPC ...................... 544/280; 514/252.16
See application file for complete search history.

(56) References Cited

U.S. PATENT DOCUMENTS

2010/0105653 A1    4/2010 Besong et al.

FOREIGN PATENT DOCUMENTS

CN          105294737      2/2016
WO      WO 2010/020675    2/2010

OTHER PUBLICATIONS

Krystof et al. Current Pharmaceutical Design, 2012, 18, 2883-2890.*
Wesierska-Gadek et al. Expert Opin. Investig. Drugs (2011) 20(12):1611-1628.*
Golub et al., Science, 286, 531-537, 1999.*
Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p4.*

(Continued)

*Primary Examiner* — Venkataraman Balasubramanian
(74) *Attorney, Agent, or Firm* — Fish & Richardson P.C.

(57) ABSTRACT

The present invention belongs to the field of pharmaceutical chemistry, and relates to a substituted pyrrolopyrimidine CDK inhibitor, in particular to a compound as shown in formula I or a pharmaceutically acceptable salt or solvate thereof, as well as a preparation method thereof and a pharmaceutical composition thereof. The present invention also relates to the use of the compound and the pharmaceutical composition thereof in the preparation of a drug for treating diseases associated with CDK inhibition. The compound according to the present invention has a marked inhibitory effect on CDK, excellent drug absorption and significantly superior oral absorption effect.

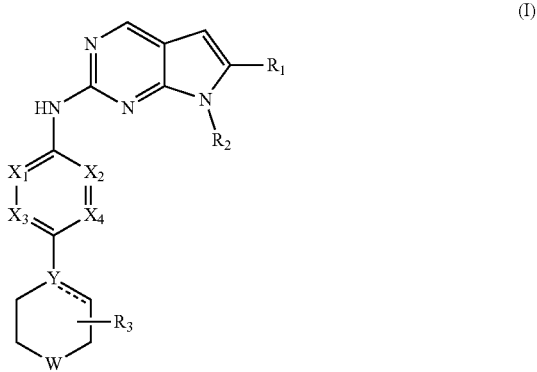

20 Claims, No Drawings

(56) References Cited

OTHER PUBLICATIONS

Dermer et al., Bio/Technology, 1994, 12:320.*
Kwapisz D. . Breast Cancer Res Treat. Nov. 2017, 166(1) 41-54. PubMed Abstract provided.*
International Search Report and Written Opinion in PCT Application PCT/CN2017/078260, dated Jun. 29, 2017, including English translation.

* cited by examiner

SUBSTITUTED PYRROLOPYRIMIDINE CDK INHIBITOR, PHARMACEUTICAL COMPOSITION CONTAINING SAME AND USE THEREOF

CROSS-REFERENCE TO RELATED APPLICATIONS

The present application claims the priority and benefit of Chinese Patent Application No. 201610180458.9 filed at the State Intellectual Property Office of China on Mar. 25, 2016, the disclosure of which is incorporated herein by reference in its entirety.

TECHNICAL FIELD

The present invention belongs to the field of pharmaceutical chemistry, relates to substituted pyrrolopyrimidine CDK inhibitors, processes for the preparation thereof and pharmaceutical compositions thereof, and also relates to use of such compounds and pharmaceutical compositions thereof in the preparation of medicaments for treating diseases associated with CDK inhibition.

BACKGROUND

A cyclin-dependent kinase (CDK) belongs to a serine/threonine protein kinase, and is mainly involved in cell cycle regulation. For example, CDK1, CDK2, CDK4 and CDK6 are involved in the regulation of cell cycle progression and checkpoint. Besides, CDK8 and CDK9 are involved in the regulation of cell transcriptional activity. Cyclin activates kinase activity of CDKs by binding to the CDKs, and phosphorylates downstream substrates to participate in the regulation of cell cycle. Different CDKs bind to specific cyclins. Wherein CDK4 and CDK6 are activated by binding to a protein of Cyclin D family, and then phosphorylate a downstream RB protein, thereby relieving the inhibitory effect of RB on a transcriptional factor E2F, and thus activating its transcriptional activity, resulting in transition of the cell cycle from G1 phase to S phase.

No matter the defect of pRB or abnormality of its regulatory factor can cause cell hyperproliferation, which is very common in tumors. About 80% tumor cells have normal pRB. In most cases, malignant proliferation of a tumor is caused by regulatory factor abnormality of a RB signal pathway. For example, excessive nucleus metastasis of a protein of cyclin D family results in inactivation of RB in mantle cell lymphoma and multiple myeloma; cyclin D is overexpressed in breast cancer and esophageal squamous cell carcinoma; CDK4 can be overexpressed in liposarcoma; and p16 has defects in melanoma, non-small cell lung cancer and pancreatic cancer. Thus, the goal of inhibiting tumor growth may be achieved by inhibiting the kinase activity of CDK4/CDK6, and its effectiveness has been validated in many cancer models in vitro and in vivo, the inhibition of its activity can block the cell cycle at G1 phase, thereby inhibiting tumor growth. Furthermore, a mouse knockout model shows that knockout of CDK4 or CDK6 has little effect on the growth and development of animals, and abnormalities occur only in individual organs, while knockout of CDK1 results in embryo deaths. Therefore, compared with a broad spectrum inhibitor of CDKs family, an inhibitor selectively targeting CDK4/CDK6 may have a greater therapeutic window.

WO2010020675 discloses a compound ribociclib (also known as LEE011) as a CDK4/CDK6 inhibitor, which is developed by Novartis, and has entered phase III clinical trials at present.

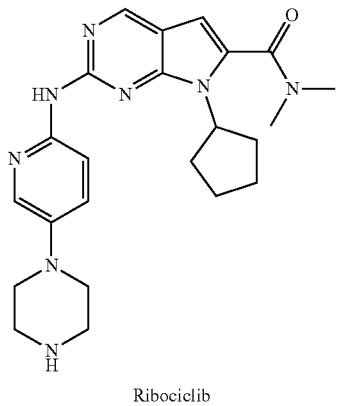 [SMILES: CN(C)C(=O)c1cc2cnc(Nc3ccc(N4CCNCC4)cn3)nc2n1C1CCCC1]

Ribociclib

SUMMARY OF THE INVENTION

In one aspect, the present invention provides a compound of Formula I or a pharmaceutically acceptable salt or solvate thereof,

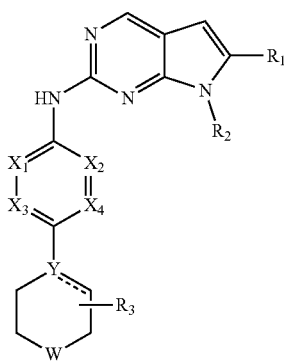

I wherein, $R_1$ is selected from the group consisting of —S(O)$_2$R$_4$ and —C(O)NR$_5$R$_6$;

$R_4$ is selected from the group consisting of hydrogen, $C_{1-6}$ alkyl, $C_{2-6}$ alkenyl, $C_{2-6}$ alkynyl, $C_{3-6}$ cycloalkyl, 3- to 6-membered heterocycloalkyl, 5- to 10-membered aryl, and 5- to 10-membered heteroaryl, which are optionally substituted by one or more $R_a$;

$R_5$ and $R_6$ are independently selected from the group consisting of hydrogen, $C_{1-6}$ alkyl, $C_{2-6}$ alkenyl, $C_{2-6}$ alkynyl, $C_{3-6}$ cycloalkyl, 3- to 6-membered heterocycloalkyl, 5- to 10-membered aryl, and 5- to 10-membered heteroaryl, which are optionally substituted by one or more $R_a$;

$R_2$ is selected from the group consisting of hydrogen, $C_{1-6}$ alkyl and $C_{3-6}$ cycloalkyl, which are optionally substituted by one or more $R_a$;

$X_1$, $X_2$, $X_3$ and $X_4$ are independently selected from the group consisting of CH and N, and one or two of $X_1$, $X_2$, $X_3$ and $X_4$ are N, and the others are CH;

the group

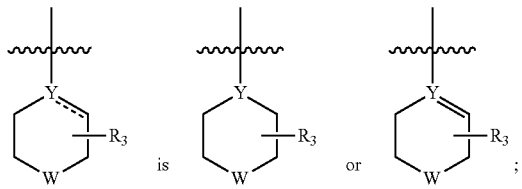

is when the group

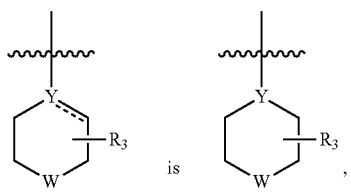

is

Y is selected from the group consisting of CH and N; and when the group

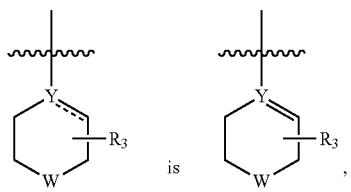

is

Y is C;

W is selected from the group consisting of O, S, $CR_7R_8$ and $NR_9$;

0-4 $R_3$ are present, $R_3$ are optionally identical or different, and $R_3$ is selected from the group consisting of $C_{1-6}$ alkyl, $C_{3-6}$ cycloalkyl, 5- to 10-membered aryl, and 5- to 10-membered heteroaryl, which are optionally substituted by one or more $R_a$;

$R_7$ and $R_8$ are independently selected from the group consisting of hydrogen, $-NR_{10}R_{11}$, $C_{1-6}$ alkyl, $C_{3-6}$ cycloalkyl, 5- to 10-membered aryl, and 5- to 10-membered heteroaryl, which are optionally substituted by one or more $R_a$;

$R_{10}$ and $R_{11}$ are independently selected from the group consisting of hydrogen, $C_{1-6}$ alkyl, $C_{3-6}$ cycloalkyl, 5- to 10-membered aryl, and 5- to 10-membered heteroaryl, which are optionally substituted by one or more $R_a$;

$R_9$ is selected from the group consisting of hydrogen, $C_{1-6}$ alkyl, $C_{3-6}$ cycloalkyl, 5- to 10-membered aryl, and 5- to 10-membered heteroaryl, which are optionally substituted by one or more $R_a$;

$R_a$ is selected from the group consisting of halogen, cyano, $-R$, $-OR$, $=O$, $-SR$, $-NR_2$, $=NR$, $-C(halogen)_3$, $-CR(halogen)_2$, $-CR_2(halogen)$, $-OCN$, $-SCN$, $-N=C=O$, $-NCS$, $-NO$, $-NO_2$, $-NRC(=O)R$, $-NRC(=O)OR$, $-NRC(=O)NRR$, $-C(=O)NRR$, $-C(=O)OR$, $-OC(=O)NRR$, $-OC(=O)OR$, $-C(=O)R$, $-S(=O)_2OR$, $-S(=O)_2R$, $-OS(=O)_2OR$, $-S(=O)_2NRR$, $-S(=O)R$, $-NRS(=O)_2R$, $-NRS(=O)_2NRR$, $-NRS(=O)_2OR$, $-OP(=O)(OR)_2$, $-P(=O)(OR)_2$, $-C(=O)R$, $-C(=S)R$, $-C(=O)OR$, $-C(=S)OR$, $-C(=O)SR$, $-C(=S)SR$, $-C(=O)NRR$, $-C(=S)NRR$, $-C(=NR)NRR$ and $-NRC(=NR)NRR$;

and R is independently selected from the group consisting of hydrogen, $C_{1-6}$ alkyl, $C_{3-6}$ cycloalkyl, 3- to 6-membered heterocycloalkyl, 5- to 10-membered aryl and 5- to 10-membered heteroaryl; and provided that: when $R_1$ is selected from $-C(O)NR_5R_6$, the group

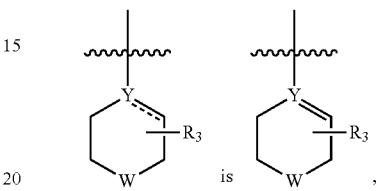

is and Y is C.

DETAILED DESCRIPTION OF THE INVENTION

In one aspect, the present invention provides a compound of Formula I or a pharmaceutically acceptable salt or solvate thereof,

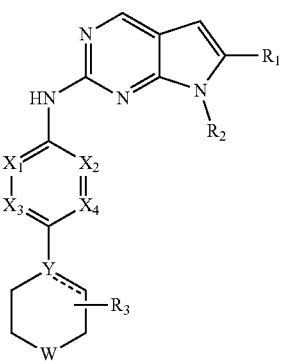

I wherein, $R_1$ is selected from the group consisting of $-S(O)_2R_4$ and $-C(O)NR_5R_6$;

$R_4$ is selected from the group consisting of hydrogen, $C_{1-6}$ alkyl, $C_{2-6}$ alkenyl, $C_{2-6}$ alkynyl, $C_{3-6}$ cycloalkyl, 3- to 6-membered heterocycloalkyl, 5- to 10-membered aryl, and 5- to 10-membered heteroaryl, which are optionally substituted by one or more $R_a$;

$R_5$ and $R_6$ are independently selected from the group consisting of hydrogen, $C_{1-6}$ alkyl, $C_{2-6}$ alkenyl, $C_{2-6}$ alkynyl, $C_{3-6}$ cycloalkyl, 3- to 6-membered heterocycloalkyl, 5- to 10-membered aryl, and 5- to 10-membered heteroaryl, which are optionally substituted by one or more $R_a$;

$R_2$ is selected from the group consisting of hydrogen, $C_{1-6}$ alkyl and $C_{3-6}$ cycloalkyl, which are optionally substituted by one or more $R_a$;

$X_1$, $X_2$, $X_3$ and $X_4$ are independently selected from the group consisting of CH and N, and one or two of $X_1$, $X_2$, $X_3$ and $X_4$ are N, and the others are CH;

the group

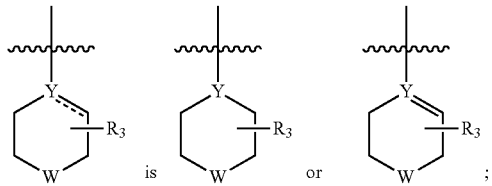

is when the group

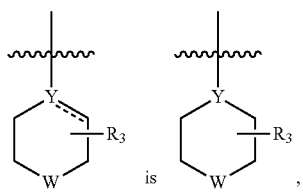

is

Y is selected from the group consisting of CH and N; and when the group

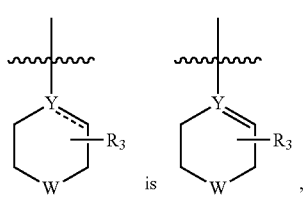

is

Y is C;

W is selected from the group consisting of O, S, $CR_7R_8$ and $NR_9$;

0-4 $R_3$ are present, $R_3$ are optionally identical or different, and $R_3$ is selected from the group consisting of $C_{1-6}$ alkyl, $C_{3-6}$ cycloalkyl, 5- to 10-membered aryl, and 5- to 10-membered heteroaryl, which are optionally substituted by one or more $R_a$;

$R_7$ and $R_8$ are independently selected from the group consisting of hydrogen, $-NR_{10}R_{11}$, $C_{1-6}$ alkyl, $C_{3-6}$ cycloalkyl, 5- to 10-membered aryl, and 5- to 10-membered heteroaryl, which are optionally substituted by one or more $R_a$;

$R_{10}$ and $R_{11}$ are independently selected from the group consisting of hydrogen, $C_{1-6}$ alkyl, $C_{3-6}$ cycloalkyl, 5- to 10-membered aryl, and 5- to 10-membered heteroaryl, which are optionally substituted by one or more $R_a$;

$R_9$ is selected from the group consisting of hydrogen, $C_{1-6}$ alkyl, $C_{3-6}$ cycloalkyl, 5- to 10-membered aryl, and 5- to 10-membered heteroaryl, which are optionally substituted by one or more $R_a$;

$R_a$ is selected from the group consisting of halogen, cyano, —R, —OR, =O, —SR, —$NR_2$, =NR, —C(halogen)$_3$, —CR(halogen)$_2$, —$CR_2$(halogen), —OCN, —SCN, —N=C=O, —NCS, —NO, —$NO_2$, —NRC(=O)R, —NRC(=O)OR, —NRC(=O)NRR, —C(=O)NRR, —C(=O)OR, —OC(=O)NRR, —OC(=O)OR, —C(=O)R, —S(=O)$_2$OR, —S(=O)$_2$R, —OS(=O)$_2$OR, —S(=O)$_2$NRR, —S(=O)R, —NRS(=O)$_2$R, —NRS(=O)$_2$NRR, —NRS(=O)$_2$OR, —OP(=O)(OR)$_2$, —P(=O)(OR)$_2$, —C(=O)R, —C(=S)R, —C(=O)OR, —C(=S)OR, —C(=O)SR, —C(=S)SR, —C(=O)NRR, —C(=S)NRR, —C(=NR)NRR and —NRC(=NR)NRR;

and R is independently selected from the group consisting of hydrogen, $C_{1-6}$ alkyl, $C_{3-6}$ cycloalkyl, 3- to 6-membered heterocycloalkyl, 5- to 10-membered aryl and 5- to 10-membered heteroaryl; and provided that: when $R_1$ is selected from —C(O)$NR_5R_6$, the group

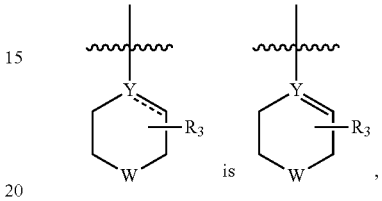

is and Y is C.

It should be understood, when W is selected from the group consisting of O, S, $CR_7R_8$ and $NR_9$, the group

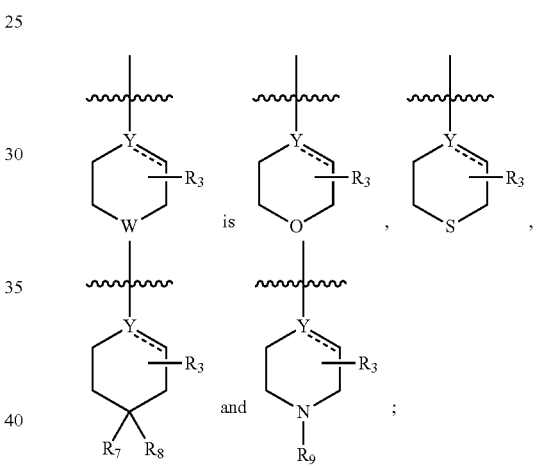

when Y is selected from the group consisting of CH and N, the group

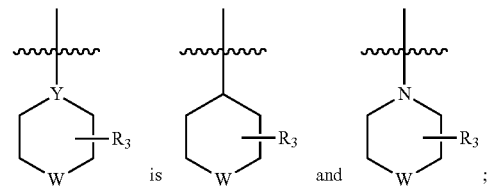

and when Y is selected from C, the group

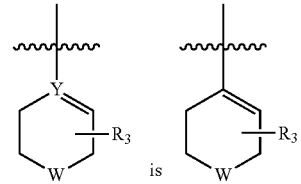

is

In some embodiments of the compound of Formula I, the pharmaceutically acceptable salt is a hydrochloride salt.

In some embodiments of the compound of Formula I, when $R_a$ is —R, R is not hydrogen.

In some embodiments of the compound of Formula I, $R_4$ is selected from the group consisting of $C_{1-6}$ alkyl and phenyl, which are optionally substituted by one or more $R_a$; in some embodiments of the compound of Formula I, $R_4$ is selected from the group consisting of $C_{1-4}$ alkyl and phenyl, which are optionally substituted by one or more $R_a$; in some embodiments of the compound of Formula I, $R_4$ is selected from the group consisting of methyl, ethyl and phenyl, which are optionally substituted by one or more $R_a$; and in some preferred embodiments of the compound of Formula I, $R_4$ is selected from the group consisting of methyl, ethyl and phenyl.

In some embodiments of the compound of Formula I, $R_5$ and $R_6$ are independently selected from $C_{1-6}$ alkyl, which is optionally substituted by one or more $R_a$; in some embodiments of the compound of Formula I, $R_5$ and $R_6$ are independently selected from $C_{1-4}$ alkyl, which is optionally substituted by one or more $R_a$; in some embodiments of the compound of Formula I, $R_5$ and $R_6$ are independently selected from the group consisting of methyl and ethyl, which are optionally substituted by one or more $R_a$; and in some preferred embodiments of the compound of Formula I, $R_5$ and $R_6$ are independently selected from methyl.

In some embodiments of the compound of Formula I, $R_2$ is selected from $C_{3-6}$ cycloalkyl, which is optionally substituted by one or more $R_a$; in some embodiments of the compound of Formula I, $R_2$ is selected from cyclopentyl, which is optionally substituted by one or more $R_a$; and in some embodiments of the compound of Formula I, $R_2$ is selected from cyclophentyl.

In some embodiments of the compound of Formula I, $X_1$, $X_2$, $X_3$ and $X_4$ are independently selected from the group consisting of CH and N, and one of $X_1$, $X_2$, $X_3$ and $X_4$ is N, and the others are CH; and in some embodiments of the compound of Formula I, $X_1$ is N, and $X_2$, $X_3$ and $X_4$ are CH. In some embodiments of the compound of Formula I, the group

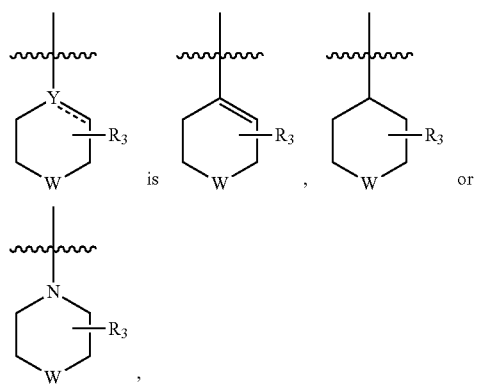

and W is selected from the group consisting of $CR_7R_8$ and $NR_9$, and preferably $CHR_8$ and $NR_9$, wherein $R_7$, $R_8$ and $R_9$ are as defined hereinbefore; in some embodiments of the compound of Formula I, the group

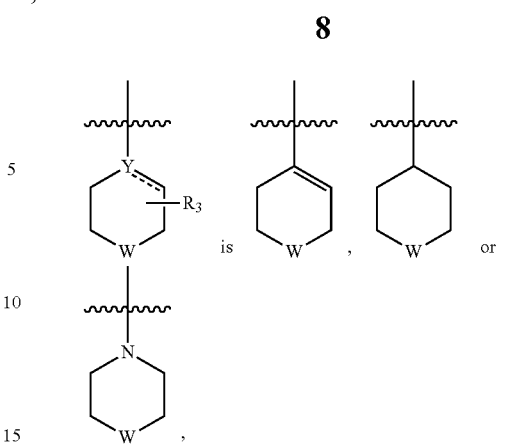

and W is selected from the group consisting of $CR_7R_8$ and $NR_9$, and preferably $CHR_8$ and $NR_9$, wherein $R_7$, $R_8$ and $R_9$ are as defined hereinbefore; in some embodiments of the compound of Formula I, the group

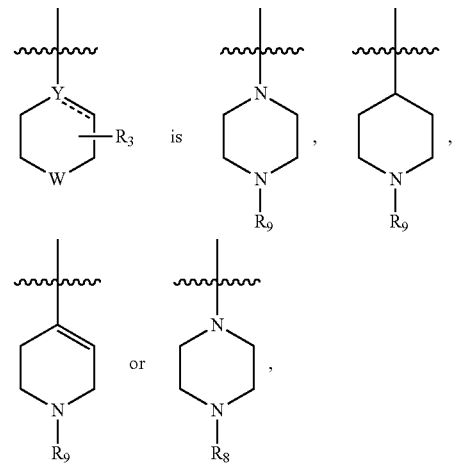

wherein $R_8$ and $R_9$ are as defined hereinbefore; and in some preferred embodiments of the compound of Formula I, the group

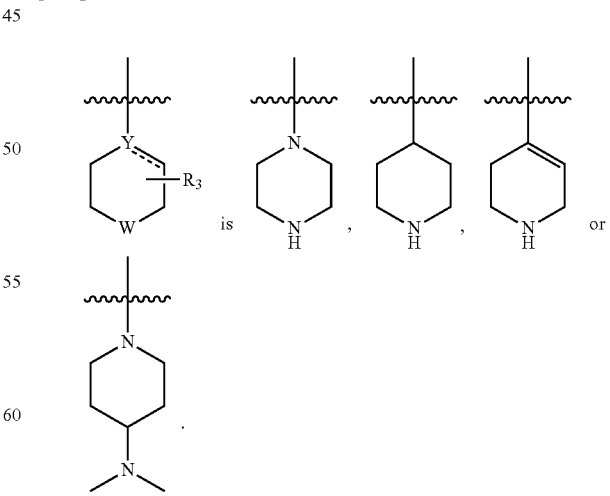

In some embodiments of the compound of Formula I, $R_7$ is hydrogen, and $R_8$ is selected from the group consisting of hydrogen, —$NR_{10}R_{11}$, $C_{1-6}$ alkyl and $C_{3-6}$ cycloalkyl, which are optionally substituted by one or more $R_a$; and in some embodiments of the compound of Formula I, $R_7$ is hydrogen, and $R_8$ is selected from —$NR_{10}R_{11}$.

In some embodiments of the compound of Formula I, $R_{10}$ and $R_{11}$ are independently selected from the group consisting of hydrogen, $C_{1-6}$ alkyl and $C_{3-6}$ cycloalkyl, which are optionally substituted by one or more $R_a$; in some embodiments of the compound of Formula I, $R_{10}$ and $R_{11}$ are independently selected from the group consisting of hydrogen and $C_{1-4}$ alkyl, which are optionally substituted by one or more $R_a$; and in some preferred embodiments of the compound of Formula I, $R_{10}$ and $R_{11}$ are independently selected from methyl.

In some preferred embodiments of the compound of Formula I, $R_7$ is hydrogen, and $R_8$ is —$N(CH_3)_2$.

In some embodiments of the compound of Formula I, $R_9$ is selected from the group consisting of hydrogen and $C_{1-4}$ alkyl, which is optionally substituted by one or more $R_a$; and in some preferred embodiments of the compound of Formula I, $R_9$ is selected from hydrogen.

In some embodiments of the compound of Formula I, 0-4 $R_3$ are present, $R_3$ are optionally identical or different, and $R_3$ is selected from $C_{1-6}$ alkyl, which is optionally substituted by one or more $R_a$; and in some preferred embodiments of the compound of Formula I, $R_3$ is not present.

In another aspect, the present invention provides a compound of Formula II or a pharmaceutically acceptable salt or solvate thereof,

II

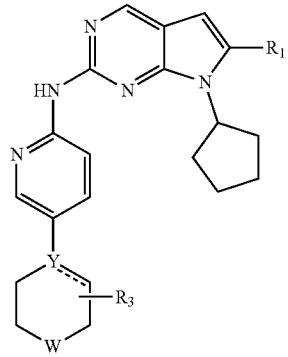

wherein $R_1$, the group

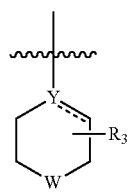

and $R_3$ are as defined hereinbefore.

In some embodiments of the compound of Formula II, the pharmaceutically acceptable salt is a hydrochloride salt.

In a further aspect, the present invention provides a compound of Formula III or a pharmaceutically acceptable salt or solvate thereof,

III

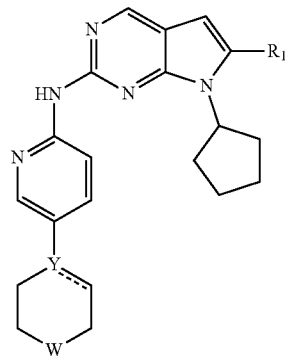

wherein,
the group

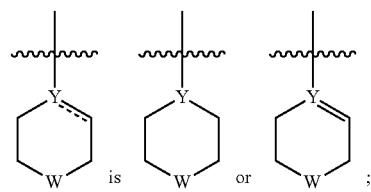

when the group

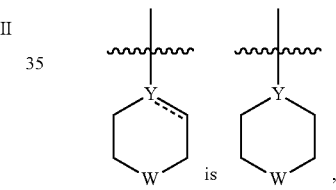

Y is selected from the group consisting of CH and N; and when the group is

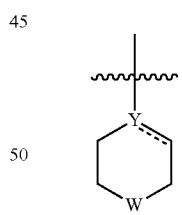

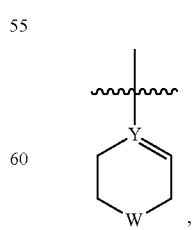

Y is C;
W is selected from the group consisting of O, S, $CR_7R_8$ and $NR_9$;

R$_1$, R$_7$, R$_8$ and R$_9$ are as defined hereinbefore; and
provided that when R$_1$ is selected from —C(O)NR$_5$R$_6$, the group

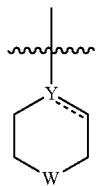

is

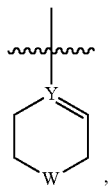

and Y is C.

In some preferred embodiments of the compound of Formula III, W is selected from the group consisting of CR$_7$R$_8$ and NR$_9$.

In some more preferred embodiments of the compound of Formula III, W is selected from the group consisting of CHR$_8$ and NR$_9$.

In some embodiments of the compound of Formula III, the group

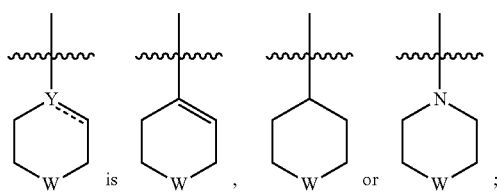

in some embodiments of the compound of Formula III, the group

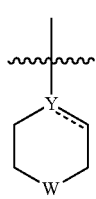

is

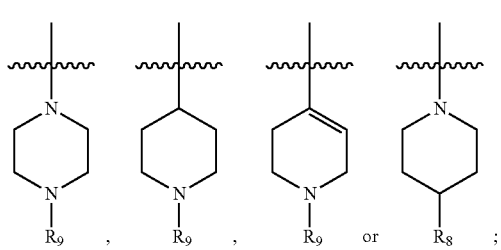

and in some preferred embodiments of the compound of Formula III, the group

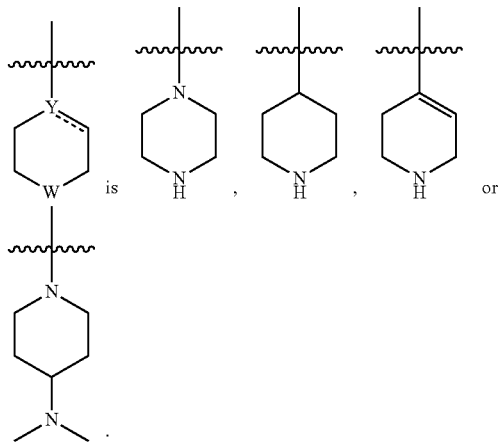

In some embodiments of the compound of Formula III, the pharmaceutically acceptable salt is a hydrochloride salt.

In still another aspect, the present invention provides a compound of Formula IV or a pharmaceutically acceptable salt or solvate thereof,

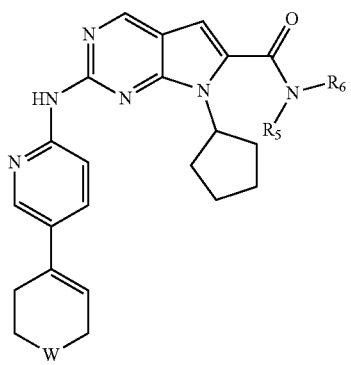

IV wherein,
W is selected from the group consisting of CR$_7$R$_8$ and NR$_9$; and
R$_5$, R$_6$, R$_7$, R$_8$ and R$_9$ are as defined hereinbefore.

In some embodiments of the compound of Formula IV, the group

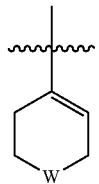

is

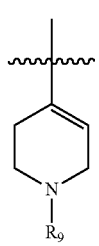

;

and in some preferred embodiments of the compound of Formula IV, the group
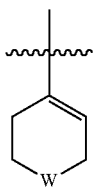
is
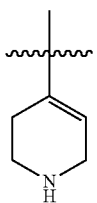
In some embodiments of the compound of Formula IV, the pharmaceutically acceptable salt is a hydrochloride salt.
In another aspect, the present invention provides the following compounds or pharmaceutically acceptable salts or solvates thereof:
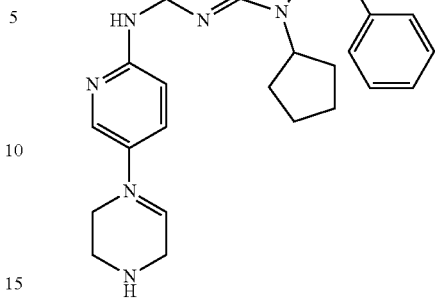
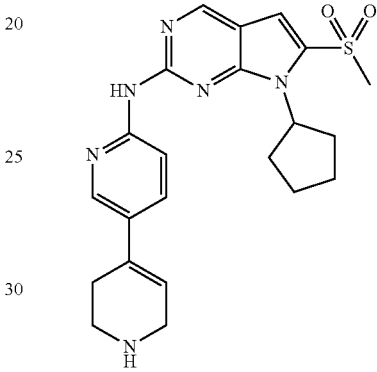
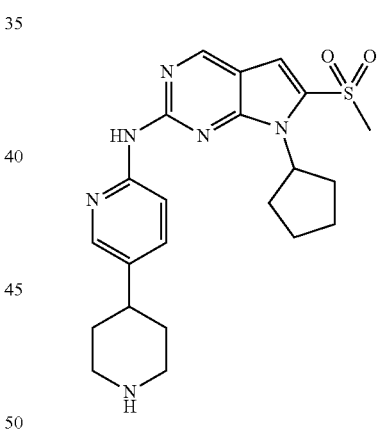
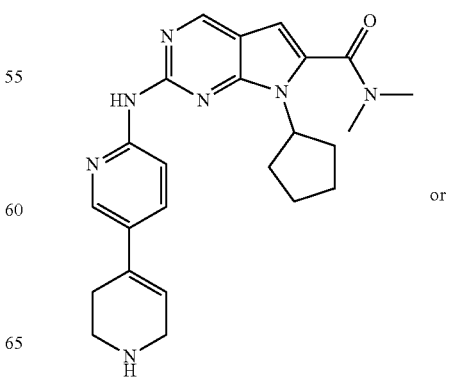
or

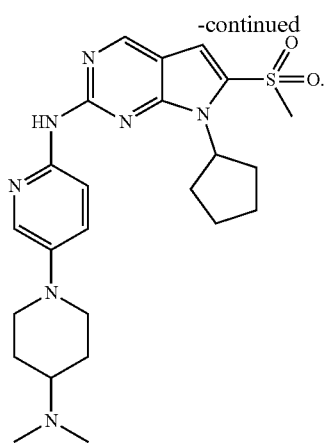

In some embodiments of the present invention, the pharmaceutically acceptable salt is a hydrochloride salt.

In still another aspect, the present invention provides the following compounds:

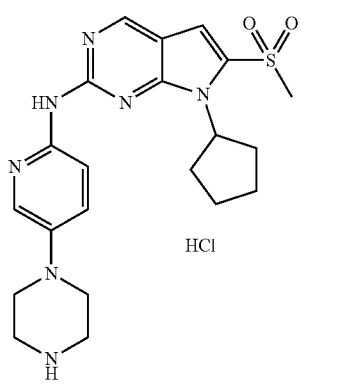

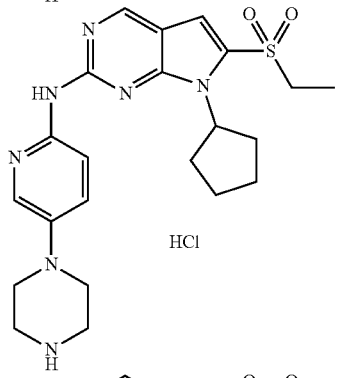

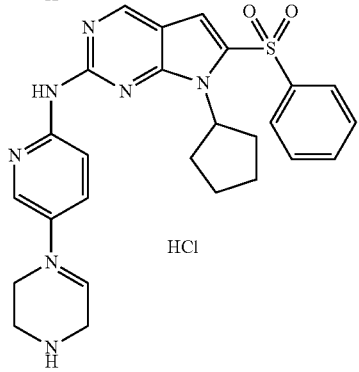

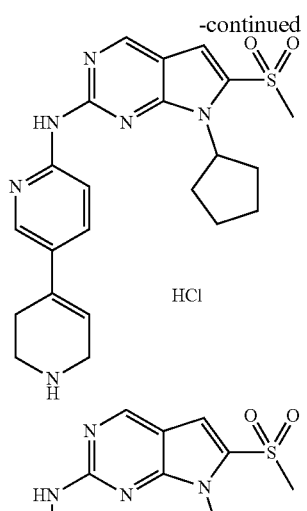

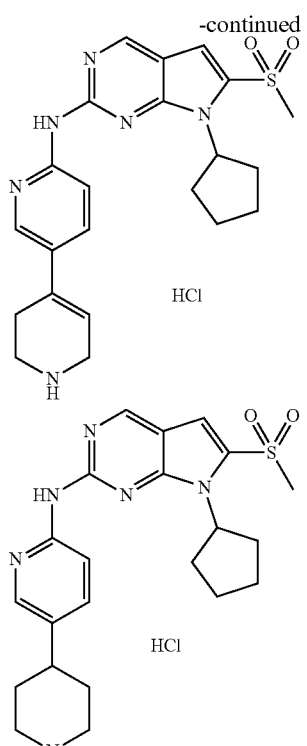

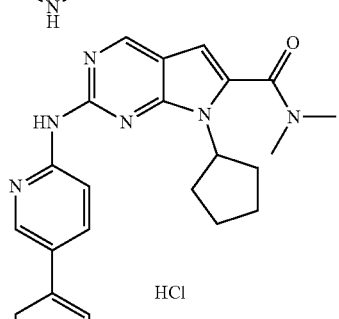

or

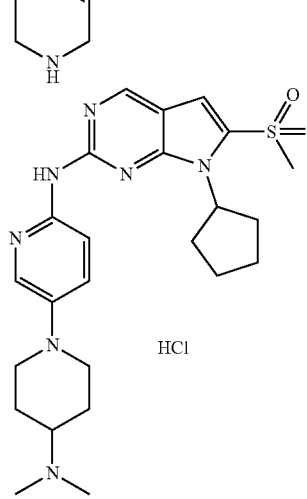

In a further aspect, the present invention provides the following compounds or pharmaceutically acceptable salts or solvates thereof:

7-cyclopentyl-6-methylsulfonyl-N-(5-(piperazin-1-yl)pyridin-2-yl)-7H-pyrrolo[2,3-d]pyrimidin-2-amine;

7-cyclopentyl-6-ethylsulfonyl-N-(5-(piperazin-1-yl)pyridin-2-yl)-7H-pyrrolo[2,3-d]pyrimidin-2-amine;

7-cyclopentyl-6-methylsulfonyl-N-(5-(4-(dimethylamino)
piperidin-1-yl)pyridin-2-yl)-7H-pyrrolo[2,3-d]pyrimidin-
2-amine;

7-cyclopentyl-6-methylsulfonyl-N-(5-(1,2,3,6-4H-pyridin-
4-yl)pyridin-2-yl)-7H-pyrrolo[2,3-d]pyrimidin-2-amine;

7-cyclopentyl-6-methylsulfonyl-N-(5-(piperidin-4-yl)pyri-
din-2-yl)-7H-pyrrolo[2,3-d]pyrimidin-2-amine;

7-cyclopentyl-6-N,N-dimethylcarbamoyl-N-(5-(1,2,3,6-4H-
pyridin-4-yl)pyridin-2-yl)-7H-pyrrolo[2,3-d]pyrimidin-
2-amine; and 7-cyclopentyl-6-phenylsulfonyl-N-(5-(piperazin-1-yl)pyri-
din-2-yl)-7H-pyrrolo[2,3-d]pyrimidin-2-amine.

In still another aspect, the present invention provides the following compounds:

7-cyclopentyl-6-methylsulfonyl-N-(5-(piperazin-1-yl)pyri-
din-2-yl)-7H-pyrrolo[2,3-d]pyrimidin-2-amine hydro-
chloride;

7-cyclopentyl-6-ethylsulfonyl-N-(5-(piperazin-1-yl)pyri-
din-2-yl)-7H-pyrrolo[2,3-d]pyrimidin-2-amine hydro-
chloride;

7-cyclopentyl-6-methylsulfonyl-N-(5-(4-(dimethylamino)
piperidin-1-yl)pyridin-2-yl)-7H-pyrrolo[2,3-d]pyrimidin-
2-amine hydrochloride;

7-cyclopentyl-6-methylsulfonyl-N-(5-(1,2,3,6-4H-pyridin-
4-yl)pyridin-2-yl)-7H-pyrrolo[2,3-d]pyrimidin-2-amine
hydrochloride;

7-cyclopentyl-6-methylsulfonyl-N-(5-(piperidin-4-yl)pyri-
din-2-yl)-7H-pyrrolo[2,3-d]pyrimidin-2-amine hydro-
chloride;

7-cyclopentyl-6-N,N-dimethylcarbamoyl-N-(5-(1,2,3,6-4H-
pyridin-4-yl)pyridin-2-yl)-7H-pyrrolo[2,3-d]pyrimidin-
2-amine hydrochloride; and 7-cyclopentyl-6-phenylsulfonyl-N-(5-(piperazin-1-yl)pyri-
din-2-yl)-7H-pyrrolo[2,3-d]pyrimidin-2-amine hydro-
chloride.

In another aspect, the present invention provides a pharmaceutical composition, comprising a therapeutically effective amount of the compound of Formula I, II, III or IV or a pharmaceutically acceptable salt or solvate thereof, and one or more pharmaceutically acceptable carriers or excipients.

The pharmaceutical composition according to the present invention may be prepared by combining the compound or a pharmaceutically acceptable salt thereof according to the present invention with a suitable pharmaceutically acceptable carrier, for example, it may be formulated into solid, semisolid, liquid or gaseous formulations, such as tablets, pills, capsules, powders, granules, ointments, emulsions, suspensions, solutions, suppositories, injections, inhalants, gels, microspheres, aerosols, and the like.

Typical routes of administration of the compound according to the present invention or the pharmaceutically acceptable salt, hydrate, solvate or prodrug thereof, or the pharmaceutical composition thereof include, but are not limited to, oral, rectal, transmucosal, enteral, or topical, transdermal, inhalation, parenteral, sublingual, intravaginal, intranasal, intraocular, intraperitoneal, intramuscular, subcutaneous, and intravenous administration.

The pharmaceutical composition according to the present invention may be manufactured by using a method well-known in the art, such as conventional mixing method, dissolution method, granulation method, dragee manufacture method, grinding method, emulsification method, lyophilization method and the like.

For oral administration, the pharmaceutical composition may be formulated by mixing an active compound with a pharmaceutically acceptable carrier well-known in the art.

Such carriers enable the compound according to the present invention to be formulated into tablets, pills, pastilles, dragees, capsules, liquids, gels, slurries, suspensions, and the like, which are used for oral administration to a patient.

A solid oral pharmaceutical composition may be prepared by a conventional mixing, filling or tabletting method. For example, it may be obtained by mixing the active compound with a solid excipient, optionally grinding the resulting mixture, if necessary, adding other appropriate auxiliaries, and then processing the mixture into granules to obtain the cores of a tablet or dragee. Appropriate auxiliaries include, but are not limited to, binders, diluents, disintegrating agents, lubricants, glidants, sweetening agents, flavoring agents, and the like, such as, microcrystalline cellulose, glucose solution, acacia mucilage, gelatin solution, sucrose and starch paste; talc, starch, magnesium stearate, calcium stearate, or stearic acid; lactose, sucrose, starch, mannitol, sorbitol, or dicalcium phosphate; silicon dioxide; cross-linked sodium carboxymethyl cellulose, pregelatinized starch, sodium starch glycollate, alginic acid, corn starch, potato starch, methyl cellulose, agar, carboxymethyl cellulose, cross-linked polyvinylpyrrolidone, and the like. The cores of a dragee may be optionally coated by using a well-known method in general pharmaceutical practice, especially using an enteric coating.

The pharmaceutical composition may also be suitable for parenteral administration, such as a sterile solution, a suspension or a lyophilized product in an appropriate unit dosage form. A suitable excipient such as a filler, a buffering agent or a surfactant can be used.

The compound of Formula I, II, III or IV or the pharmaceutically acceptable salt or solvate thereof according to the present invention may be administered by any suitable route and method, such as by oral or parenteral (e.g., intravenous) administration. A therapeutically effective amount of the compound of Formula I, II, III or IV is about 0.0001 to 20 mg/Kg body weight/day, for example, 0.001 to 10 mg/Kg body weight/day.

The dosage frequency of the compound of Formula I, II, III or IV depends on the needs of a patient subject, e.g., once daily or twice daily, or more times daily. The administration may be intermittent, for example, a patient receives a daily dosage of the compound of Formula I during a period of several days, but then does not receive a daily dosage of the compound of Formula I, II, III or IV during a period of several or more days.

In another aspect, the present invention provides a method for treating and/or preventing a disease associated with CDK inhibition, comprising administering to a subject in need thereof a therapeutically effective amount of a compound of Formula I, II, III or IV or a pharmaceutically acceptable salt or solvate thereof, or a pharmaceutical composition comprising a compound of Formula I, II, III or IV or a pharmaceutically acceptable salt or solvate thereof; preferably, the disease associated with CDK inhibition refers to a disease associated with CDK4 and/or CDK6 inhibition; and in some embodiments of the present invention, the disease associated with CDK4 and/or CDK6 inhibition includes cancer.

In yet another aspect, the present invention provides use of a compound of Formula I, II, III or IV or a pharmaceutically acceptable salt or solvate thereof, or a pharmaceutical composition comprising the compound of Formula I, II, III or IV or a pharmaceutically acceptable salt or solvate thereof in the preparation of a medicament for treating and/or preventing a disease associated with CDK inhibition; preferably, the disease associated with CDK inhibition refers to a disease associated with CDK4 and/or CDK6 inhibition; and in some embodiments of the present invention, the disease associated with CDK4 and/or CDK6 inhibition includes cancer.

In still another aspect, the present invention provides a method for treating and/or preventing cancer, comprising administering to a subject in need thereof a therapeutically effective amount of a compound of Formula I, II, III or IV or a pharmaceutically acceptable salt or solvate thereof, or a pharmaceutical composition comprising a compound of Formula I, II, III or IV or a pharmaceutically acceptable salt or solvate thereof.

In a further aspect, the present invention provides use of a compound of Formula I, II, III or IV or a pharmaceutically acceptable salt or solvate thereof, or a pharmaceutical composition comprising a compound of Formula I, II, III or IV or a pharmaceutically acceptable salt or solvate thereof, in the preparation of a medicament for treating and/or preventing cancer.

In some embodiments of the present invention, the cancer includes, but is not limited to: bladder cancer; breast cancer, e.g., metastatic breast cancer; colon cancer; kidney cancer; epidermal cancer; liver cancer; lung cancer, e.g., small cell lung cancer and non-small cell lung cancer; esophageal cancer; gallbladder cancer; ovarian cancer; pancreatic cancer, e.g., exocrine pancreatic cancer; gastric cancer; cervical cancer; thyroid cancer; rhinocarcinoma; head and neck cancer; prostate cancer; skin cancer, e.g., squamous cell carcinoma; lymphoid hematopoietic cell tumor, e.g., leukemia, acute lymphoblastic leukemia, chronic lymphocytic leukemia, B-cell lymphoma, T-cell lymphoma, multiple myeloma, Hodgkin lymphoma, non-Hodgkin lymphoma, hair cell lymphoma, and Burkitt lymphoma; myeloid hematopoietic cell tumor, e.g., acute and chronic myeloid leukemia, myelodysplastic syndrome, and promyelocytic leukemia; thyroid follicular cancer; a tumor of mesenchymal origin, e.g., fibrosarcoma, and rhabdomyosarcoma; central or peripheral nervous system tumour, e.g., astrocytoma, neuroblastoma, glioma, and schwannoma; melanoma; seminoma; teratoma; osteosarcoma; xeroderma pigmentosum; keratoacanthoma; thyroid follicular cancer; liposarcoma; neuroendocrine tumor; and Kaposi sarcoma.

In some preferred embodiments of the present invention, the cancer is selected from the group consisting of metastatic breast cancer, melanoma, non-small cell lung cancer, teratoma, neuroendocrine tumor and liposarcoma.

The compounds of the present invention have a significant inhibiting effect on CDK (CDK4/CDK6), a significant inhibiting effect on proliferation of cancer cells, excellent pharmacokinetic absorption, and a significantly superior oral absorption effect.

In still another aspect, the present invention provides a method for preparing a compound of Formula I, including but not limited to the following synthesis schemes:

Synthesis Scheme 1:

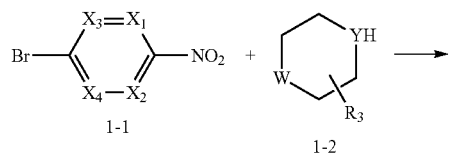

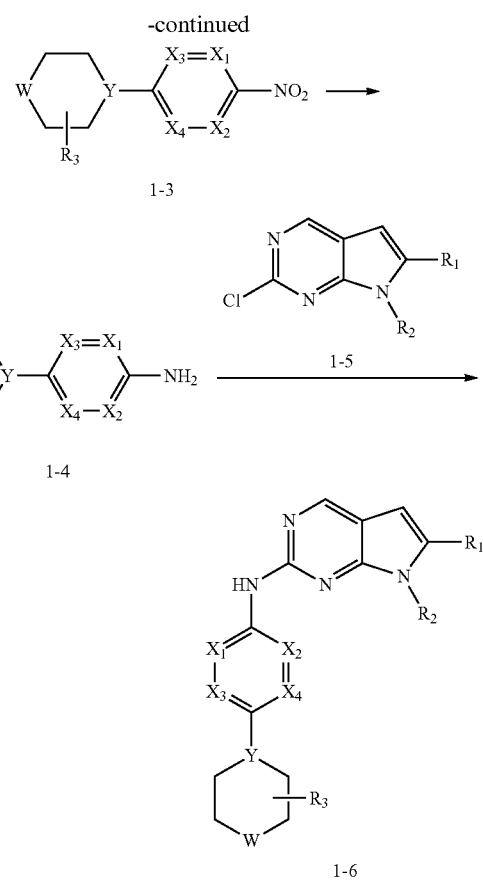

wherein,

Y is N;

$X_1$, $X_2$, $X_3$, $X_4$, $R_1$, $R_2$, $R_3$ and W are as defined hereinbefore, and W is not NH, reacting a compound of Formula 1-1 with a compound of Formula 1-2 in the presence of a solvent (e.g., DMSO) and an alkali (e.g., potassium carbonate) to prepare a compound of Formula 1-3, reacting the compound of Formula 1-3 in the presence of a catalyst (e.g., 10% Pd/C) and a reductant (e.g., hydrogen) to prepare a compound of Formula 1-4, and reacting the compound of Formula 1-4 with a compound of Formula 1-5 (e.g., in the presence of tris(dibenzylidene acetone)dipalladium, binaphthyldiphenyl phosphate, and cesium carbonate) to prepare a compound of Formula 1-6.

Synthesis Scheme 2:

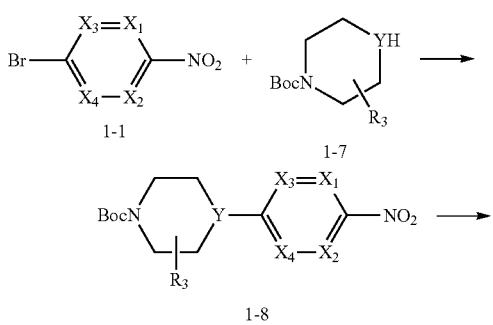

-continued

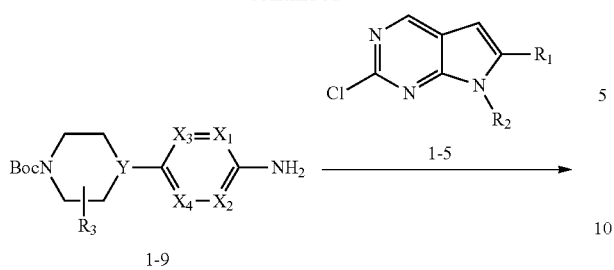
1-9

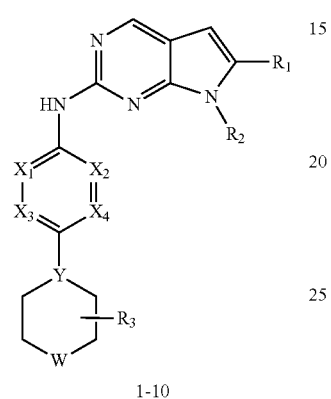
1-10 wherein,

Y is N;

$X_1$, $X_2$, $X_3$, $X_4$, $R_1$, $R_2$ and $R_3$ are as defined hereinbefore, and W is NH, reacting the compound of Formula 1-1 with a compound of Formula 1-7 in the presence of a solvent (e.g., DMSO) and an alkali (e.g., potassium carbonate) to prepare a compound of Formula 1-8, reacting the compound of Formula 1-8 in the presence of a catalyst (e.g., 10% Pd/C) and a reductant (e.g., hydrogen) to prepare a compound of Formula 1-9, and reacting the compound of Formula 1-9 with the compound of Formula 1-5 (e.g., in the presence of tris(dibenzylidene acetone)dipalladium, binaphthyldiphenyl phosphate, and cesium carbonate) to prepare a compound of Formula 1-10.

Synthesis Scheme 3:

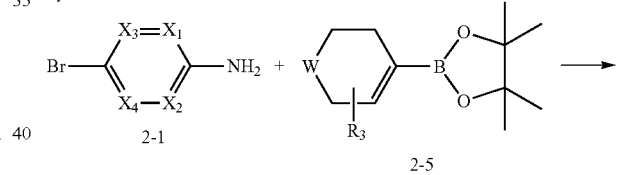

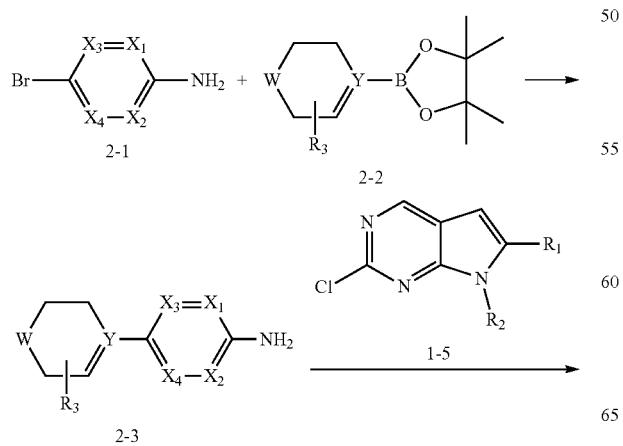

-continued

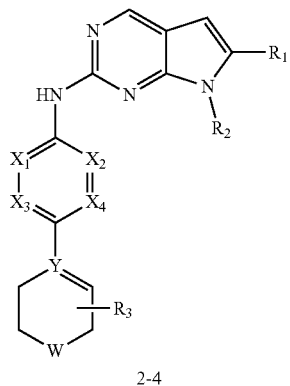
2-4 wherein,

Y is C;

$X_1$, $X_2$, $X_3$, $X_4$, $R_1$, $R_2$, $R_3$ and W are as defined hereinbefore, and W is not NH, reacting a compound of Formula 2-1 with a compound of Formula 2-2 in the presence of a catalyst (e.g., tetrakis(triphenylphosphine)palladium) and an alkali (e.g., sodium carbonate) to prepare a compound of Formula 2-3, and reacting the compound of Formula 2-3 with the compound of Formula 1-5 (e.g., in the presence of tris(dibenzylideneacetone)dipalladium, binaphthyldiphenyl phosphate, and cesium carbonate) to prepare a compound of Formula 2-4.

Synthesis Scheme 4:

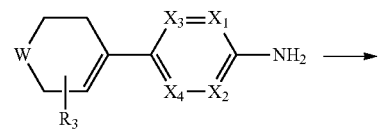

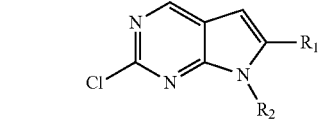

-continued

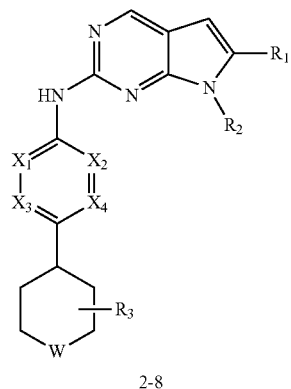

2-8 wherein $X_1$, $X_2$, $X_3$, $X_4$, $R_1$, $R_2$, $R_3$ and W are as defined hereinbefore, and W is not NH, reacting the compound of Formula 2-1 with a compound of Formula 2-5 in the presence of a catalyst (e.g., tetrakis(triphenylphosphine)palladium) and an alkali (e.g., sodium carbonate) to prepare a compound of Formula 2-6, reacting the compound of Formula 2-6 in the presence of a catalyst (e.g., 10% Pd/C) and a reductant (e.g., hydrogen) to prepare a compound of Formula 2-7, and reacting the compound of Formula 2-7 with the compound of Formula 1-5 (e.g., in the presence of tris(dibenzylideneacetone)dipalladium, binaphthyldiphenyl phosphate, and cesium carbonate) to prepare a compound of Formula 2-8.

-continued

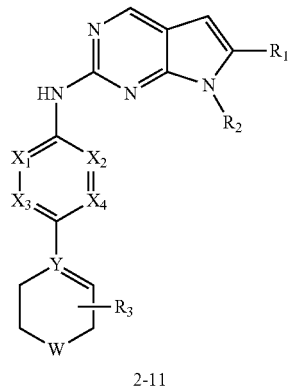

2-11 wherein,

Y is C;

wherein $X_1$, $X_2$, $X_3$, $X_4$, $R_1$, $R_2$ and $R_3$ are as defined hereinbefore, and W is NH, reacting the compound of Formula 2-1 with a compound of Formula 2-9 in the presence of a catalyst (e.g., tetrakis(triphenylphosphine)palladium) and an alkali (e.g., sodium carbonate) to prepare a compound of Formula 2-10, and reacting the compound of Formula 2-10 with the compound of Formula 1-5 (e.g., in the presence of tris(dibenzylideneacetone)dipalladium, binaphthyldiphenyl phosphate, and cesium carbonate) to prepare a compound of Formula 2-11.

Synthesis Scheme 5:

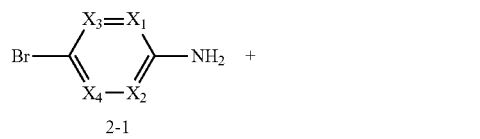

2-1

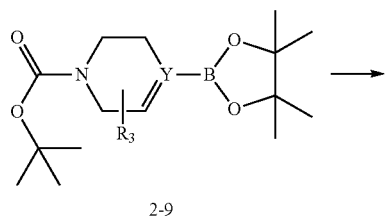

2-9

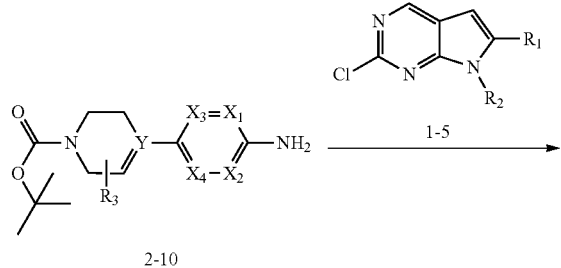

2-10

Synthesis Scheme 6:

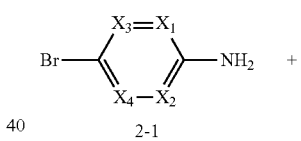

2-1

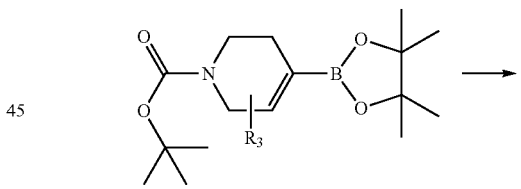

2-12

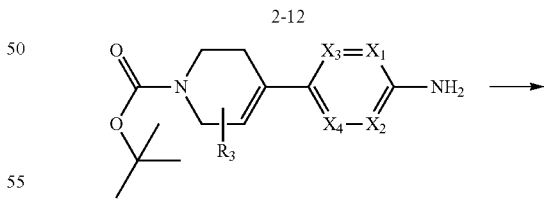

2-13

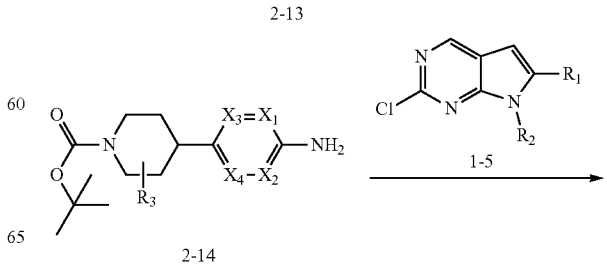

2-14

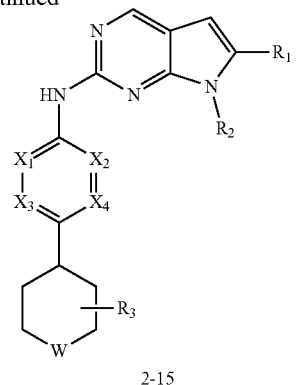

2-15 wherein $X_1$, $X_2$, $X_3$, $X_4$, $R_1$, $R_2$ and $R_3$ are as defined hereinbefore, and W is NH, reacting the compound of Formula 2-1 with a compound of Formula 2-12 in the presence of a catalyst (e.g., tetrakis(triphenylphosphine)palladium) and an alkali (e.g., sodium carbonate) to prepare a compound of Formula 2-13, reacting the compound of Formula 2-13 in the presence of a catalyst (e.g., 10% Pd/C) and a reductant (e.g., hydrogen) to prepare a compound of Formula 2-14, and reacting the compound of Formula 2-14 with the compound of Formula 1-5 (e.g., in the presence of tris(dibenzylideneacetone)dipalladium, binaphthyldiphenyl phosphate, and cesium carbonate) to prepare a compound of Formula 2-15.

Synthesis Scheme 7:

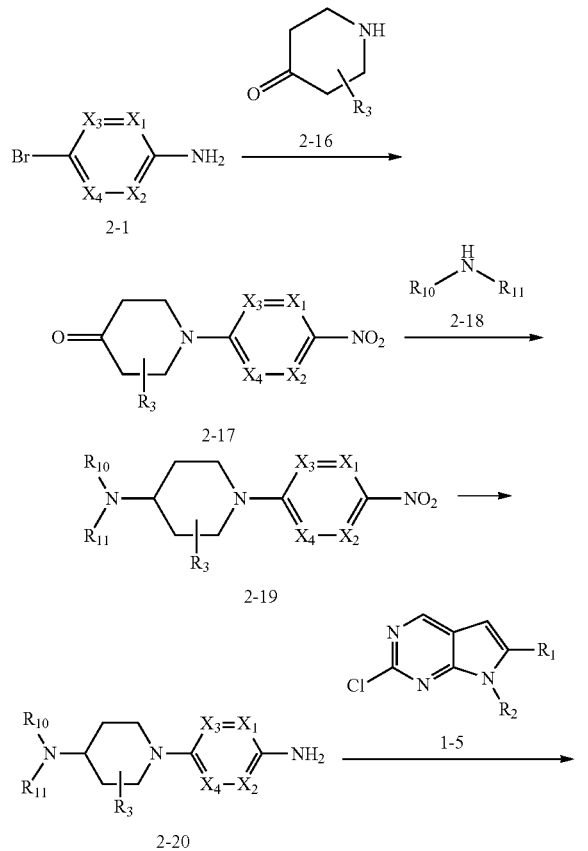

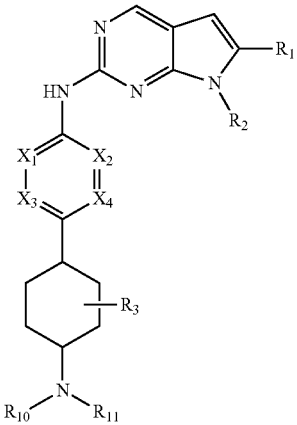

2-21 wherein $X_1$, $X_2$, $X_3$, $X_4$, $R_1$, $R_2$, $R_3$, $R_{10}$ and $R_{11}$ are as defined hereinbefore, reacting the compound of Formula 2-1 with a compound of Formula 2-16 in the presence of an alkali (e.g., potassium carbonate) to prepare a compound of Formula 2-17, reacting the compound of Formula 2-17 with a compound of Formula 2-18 (e.g., in the presence of sodium triacetoxyborohyride) to prepare a compound of Formula 2-19, reacting the compound of Formula 2-19 in the presence of a catalyst (e.g., 10% Pd/C) and a reductant (e.g., hydrogen) to prepare a compound of Formula 2-20, and reacting the compound of Formula 2-20 with the compound of Formula 1-5 (e.g., in the presence of tris(dibenzylideneacetone)dipalladium, binaphthyldiphenyl phosphate, and cesium carbonate) to prepare a compound of Formula 2-21.

Synthesis Scheme 8:

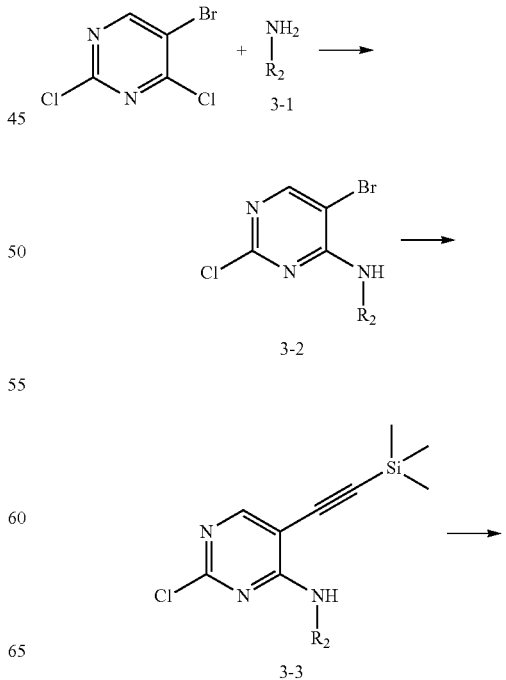

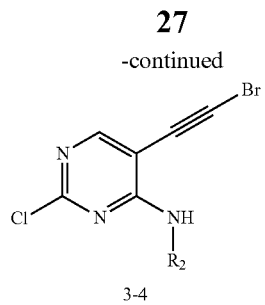

wherein R₂ is as defined hereinbefore, reacting 5-bromo-2,6-dichloropyrimidine with a compound of Formula 3-1 in the presence of diisopropyl ethylamine to prepare a compound of Formula 3-2, reacting the compound of Formula 3-2 with trimethylsilylacetylene (e.g., in the presence of triethylamine, bis(triphenylphosphine) palladium dichloride and cuprous iodide) to prepare a compound of Formula 3-3, reacting the compound of Formula 3-3 with a halogenating reagent (e.g., N-bromobutanimide) (e.g. in the presence of silver nitrate) to prepare a compound of Formula 3-4, and reacting the compound of Formula 3-4 (e.g., in the presence of tetrabutylammonium fluoride trihydrate) to prepare a compound of Formula 3-5.

Synthesis Scheme 9:

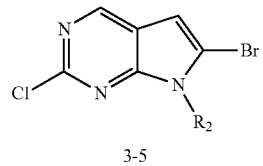

wherein R₂ and R₄ are as defined hereinbefore, reacting the compound of Formula 3-5 with a compound of Formula 3-6 (e.g., in the presence of cuprous iodide) to prepare a compound of Formula 3-7.

Synthesis Scheme 10:

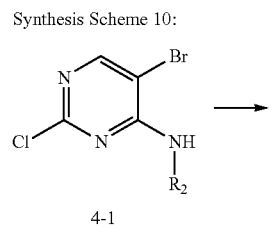

wherein R₂, R₅ and R₆ are as defined hereinbefore, reacting a compound of Formula 4-1 with propynol (e.g., in the presence of tetrabutylammonium fluoride trihydrate and [1,1'-bis(diphenylphosphino)ferrocene-palladium dichloride dichloromethane complex) to prepare a compound of Formula 4-2, reacting the compound of Formula 4-2 (e.g., in the presence of tetrabutylammonium fluoride trihydrate) to prepare a compound of Formula 4-3, and reacting the compound of Formula 4-3 with a compound of Formula 4-4 (e.g., in the presence of manganese dioxide) to prepare a compound of Formula 4-5.

Synthetic methodologies that make up the present invention are shown in the above schemes. These schemes are intended to describe the applicable chemistry through the use of specific examples, and are not indicative of the scope of the present invention or intended to limit the invention. The chemical structures in the synthesis schemes herein depict variables that are hereby defined commensurately with chemical group definitions of the corresponding position in the compound formulae herein, whether identified by the same variable name (i.e., R₁, R₂, R₃, etc.) or not. The suitability of a chemical group in a chemical structure for use in the synthesis of another compound is within the knowledge of one of ordinary skill in the art.

Definitions

As used herein, the term "compound" includes all stereoisomers, geometric isomers and tautomers.

Compounds of the present invention may be asymmetric, e.g., having one or more stereoisomers. Unless otherwise indicated, all the stereoisomers, such as enantiomers and diastereoisomers, are included within the scope of the present invention. The compounds containing asymmetric carbon atom(s) of the present invention may be isolated in an optically active pure form or a racemic form. The optically active pure form may be resolved from a racemic mixture, or synthesized from chiral starting material(s) or chiral reagent(s).

Compounds of the present invention also include tautomeric forms. The tautomeric forms are derived from the switching of a single bond and an adjacent double bond accompanied by the migration of a proton.

The term "optional" or "optionally" means that the subsequently described event or circumstance may or may not occur, and that the description includes instances where said event or circumstance occurs, and instances in which it does not. For example, "optionally substituted alkyl" defined hereinafter refers to "alkyl" or "substituted alkyl". Furthermore, an optionally substituted group may be unsubstituted (e.g., $CH_2CH_3$), fully substituted (e.g., $CF_2CF_3$), or mono-substituted (e.g., $CH_2CH_2F$), or substituted at a level anywhere in-between fully substituted and mono-substituted (e.g., $CH_2CHF_2$, $CF_2CH_3$, $CFHCHF_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

The term "heteroatom" or "hetero" refers to an atom other than carbon and hydrogen. The heteroatom is independently selected from among oxygen, nitrogen, sulfur, phosphorus, silicon, selenium and stannum, but is not limited to these atoms. In embodiments in which two or more heteroatoms are present, the two or more heteroatoms can be the same as each another, or some or all of the two or more heteroatoms can each be different from the others.

A numerical range herein refers to each integer in the given range. For example, "$C_{1-6}$" means that a group may have 1 carbon atom, 2 carbon atoms, 3 carbon atoms, 4 carbon atoms, 5 carbon atoms or 6 carbon atoms; "$C_{2-6}$" means that a group may have 2 carbon atoms, 3 carbon atoms, 4 carbon atoms, 5 carbon atoms or 6 carbon atoms; and "$C_{3-6}$" means that a group may have 3 carbon atoms, 4 carbon atoms, 5 carbon atoms or 6 carbon atoms. The term "substituted" means that one or more hydrogen atoms on a given atom are replaced with a substituent, provided that the given atom has a normal valence state and the compound after substitution is stable. When the substituent is a keto (i.e., =O), which means that two hydrogen atoms are replaced, the keto substitution will not occur on an aromatic group.

Unless otherwise specified, the term "hetero" means a heteroatom or a heteroatom group (i.e., a group containing a heteroatom), i.e., atoms other than carbon and hydrogen atoms or an atom group containing such atoms. A heteroatom is independently selected from the group consisting of oxygen, nitrogen, sulfur, phosphorus, silicon, germanium, aluminum and boron. In an embodiment where two or more heteroatoms are involved, the two or more heteroatoms may be identical, or parts or all of the two or more heteroatoms may be different.

The term "halo" or "halogen" refers to fluoro, chloro, bromo and iodo.

The term "cyano" refers to a —CN group.

The term "alkyl" refers to an optionally substituted straight-chain, or optionally substituted branched-chain monoradical saturated hydrocarbon. "Alkyl" as used herein may have from 1 to about 18 carbon atoms, or 1 to about 10 carbon atoms, preferably 1 to 6 carbon atoms. The term "lower alkyl" as used herein, alone or in combination, refers to an alkyl having relatively less carbon atoms, for example having 1 to about 8 carbon atoms, preferably having 1 to about 6 carbon atoms, or 1 to about 4 carbon atoms. Examples of alkyl as used herein include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever a numerical range appears herein, for example, "$C_{1-6}$ alkyl" means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. For example, "$C_{1-4}$ alkyl" means that the alkyl may consist of 1 carbon atom, 2 carbon atoms, 3 carbon atoms or 4 carbon atoms, and specifically refers to methyl, ethyl, n-propyl, isopropyl, n-butyl, isobutyl, sec-butyl or tert-butyl.

The term "alkenyl" refers to an optionally substituted straight or optionally substituted branched monovalent hydrocarbon, having one or more carbon-carbon double bonds. The alkenyl, for example, has 2 to about 18 carbon atoms, or has 2 to about 10 carbon atoms, and more preferably has 2 to about 6 carbon atoms. The double bonds in these groups may be in cis- or trans-configuration, and should be understood to comprise the two isomers. Where a numerical range is present herein, for example, "$C_{2-6}$ alkenyl" refers to an alkenyl that may consist of 2 carbon atoms, 3 carbon atoms, 4 carbon atoms, 5 carbon atoms or 6 carbon atoms. Non-limiting examples of the alkenyl include, but are not limited to, ethenyl, 1-propenyl, 2-propenyl, 1-butenyl, isobutenyl, 1,3-butadienyl, and the like.

The term "alkynyl" refers to an optionally substituted straight or optionally substituted branched monovalent hydrocarbon, having one or more carbon-carbon triple bonds. For example, the alkynyl has 2 to about 18 carbon atoms, or 2 to about 10 carbon atoms, and more preferably has 2 to about 6 carbon atoms. Where a numerical range is present herein, for example, "$C_{2-6}$ alkenyl" refers to an alkenyl that may consist of 2 carbon atoms, 3 carbon atoms, 4 carbon atoms, 5 carbon atoms or 6 carbon atoms. Non-limiting examples of the alkynyl include, but are not limited to, ethynyl (—C≡CH), 1-propynyl (—C≡C—$CH_3$), 2-propynyl (—$CH_2$—C≡CH), 1,3-butadiynyl (—C≡C—C≡CH), and the like.

The term "membered" refers to the number of skeletal atoms forming a ring. For example, "3- to 6-membered" means that the number of skeletal atoms forming a ring is 3, 4, 5 or 6; "5- to 10-membered" means that the number of skeletal atoms forming a ring is 5, 6, 7, 8, 9 or 10. Therefore, for example, cyclohexane, pyridine, pyran and pyrimidine are six-membered rings, while cyclopentane, pyrrole, tetrahydrofuran and thiophene are five-membered rings.

The term "cycloalkyl" refers to a saturated or unsaturated non-aromatic cyclic alkyl consisting of carbon atoms and hydrogen atoms, preferably containing 1 or 2 rings. The cycloalkyl may be a monocyclic, fused polycyclic, bridged cyclic or spirocyclic structure. Non-limiting examples of the cycloalkyl include, but are not limited to, cyclopropyl, cyclobutyl, cyclopentyl, cyclohexyl, cycloheptyl, bicyclo[2.2.1]heptyl, spiro[3.3]heptyl, and the like.

The term "heterocycloalkyl" refers to a non-aromatic monocyclic, fused polycyclic, bridged cyclic or spirocyclic group, wherein a part of ring atoms are heteroatoms selected from the group consisting of N, O and S(O)$_n$ (wherein n is 0, 1 or 2), and the remaining ring atoms are C. Such a ring may be saturated or unsaturated (for example, having one or more double bonds), but does not have a fully conjugated π-electron system. Examples of a 3-membered heterocycloalkyl include, but are not limited to, oxiranyl, cyclothioethyl, and aziridinyl; examples of a 4-membered heterocycloalkyl include, but are not limited to, azetidinyl, oxetanyl, and thietanyl; examples of a 5-membered heterocycloalkyl include, but are not limited to, tetrahydrofuranyl, tetrahydrothienyl, pyrrolidinyl, isooxazolidinyl, oxazolidinyl, isothiazolidinyl, 1,1-dioxoisothiazolidinyl, thiazolidinyl, imidazolidinyl, tetrahydropyrazolyl, pyrrolinyl, dihydrofuranyl, and dihydrothienyl; and examples of a 6-membered heterocycloalkyl include, but are not limited to, piperidinyl, tetrahydropyranyl, tetrahydrothiopyranyl, morpholinyl, piperazinyl, 1,4-thioxanyl, 1,4-dioxanyl, thiomorpholinyl, 1,2-dithioalkyl, 1,4-dithioalkyl, dihydropyridyl, tetrahydropyridyl, dihydropyranyl, tetrahydropyranyl, dihydrothiopyranyl, and the like.

The term "aryl" refers to an all-carbon monocyclic or fused polycyclic aromatic group having a conjugated π-electron system. For example, an aryl may have 6-20 carbon atoms, 6-14 carbon atoms, or 6-10 carbon atoms. Non-limiting examples of the aryl include, but are not limited to, phenyl, naphthyl, anthryl, and the like.

The term "heteroaryl" refers to a monocyclic or fused polycyclic ring system containing at least one ring atom selected from the group consisting of N, O and S, the remaining ring atoms being C, and having at least one aromatic ring. Non-limiting examples of the heteroaryl include, but are not limited to, pyrrolyl, furanyl, thienyl, imidazolyl, oxazolyl, pyrazolyl, pyridinyl, pyrimidinyl, pyrazinyl, quinolinyl, isoquinolinyl, tetrazolyl, triazolyl, triazinyl, benzofuranyl, benzothienyl, indolyl, isoindolyl, and the like.

The term "solvate" refers to a combination of a compound according to the present invention and a solvent molecule formed by solvation.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "pharmaceutically acceptable salt" refers to a salt that retains the biological effectiveness of the free acids and free bases of a specific compound, without adverse biological effects. For example, the salt may be an acid (including an organic acid and an inorganic acid) addition salt or a base (including an organic base and an inorganic base) addition salt. In some embodiments of the present invention, the pharmaceutically acceptable salt is a hydrochloride salt.

The pharmaceutical acceptable salt according to the present invention may be synthesized from a parent compound that contains an acidic or basic moiety by conventional chemical methods. Generally, such salts can be prepared by reacting the free acid or base forms of these compounds with a stoichiometric amount of an appropriate base or acid in water, an organic solvent, or a mixture of the two.

The term "pharmaceutically acceptable carrier" refers to those carriers which have no significant irritation to an organism and do not impair the bioactivity and property of the active compound. The "pharmaceutically acceptable carrier" refers to an inert substance which is administered with an active ingredient and is beneficial to the administration of the active ingredient, and includes but not limited to any of the following substances which are acceptable for use in humans or animals (e.g. livestocks) approved by the State Food and Drug Administration: glidants, sweetening agents, diluents, preservatives, dyes/colorants, flavoring agents, surfactants, wetting agents, dispersants, disintegrants, suspending agents, stabilizing agents, isotonic agents, solvents or emulsifying agents. Non-limiting examples of the carriers comprise calcium carbonate, calcium phosphate, various sugars and various starches, cellulose derivatives, gelatines, vegetable oil, polyethylene glycol and the like. Other information regarding the carriers may refer to Remington: The Science and Practice of Pharmacy, 21st Ed., Lippincott, Williams & Wilkins (2005), the content of which is incorporated herein by reference.

The term "excipient" usually refers to a carrier, diluent and/or medium required for the preparation of an effective pharmaceutical composition.

The term "treating" or "treatment" means that the compound or formulation of the present application is administrated to prevent, ameliorate or eliminate diseases, or one or more symptoms associated with said diseases, and comprises:

(i) preventing the occurrence of a disease or condition in mammals, particularly when such mammals are susceptible to the condition, but have not yet been diagnosed as suffering from said condition;

(ii) inhibiting a disease or condition, i.e., suppressing the development of the disease or condition;

(iii) alleviating a disease or condition, i.e., causing the regression of the disease or condition.

For a drug or pharmacological active agent, the term "effective amount" or "therapeutically effective amount" refers to a sufficient amount of a drug or formulation that can achieve desired effects but is non-toxic. For the oral dosage form of the present invention, "an effective amount" of an active substance in a composition refers to an amount required to achieve desired effects when the active substance is combined with another active substance in the composition. The determination of an effective amount varies from person to person, depending on the age and the general condition of a subject, and also depending on the specific active substance. An appropriate effective amount in individual cases can be determined by the person skilled in the art according to conventional tests.

The term "patient" or "subject" includes human and animals, such as mammals (such as primates, cows, horses, pigs, dogs, cats, mouse, rats, rabbits, goats, sheep and poultry, etc.).

The term "pharmaceutical composition" refers to a mixture of one or more of the compounds or salts thereof according to the present application and a pharmaceutically acceptable excipient. An object of the pharmaceutical composition is to facilitate administering the compound according to the present application to an organism.

The term "comprise" and English variations thereof (such as comprises or comprising) should be understood as open and non-exclusive meanings, i.e. "including but not limited to".

The intermediates and compounds according to the present application may also exist in the form of different tautomers, and all such forms are included in the scope of the present application. The term "tautomer" or "tautomeric form" refers to structural isomers of different energies which are interconvertible via a low energy barrier. For example, proton tautomers (also known as prototropic tautomers)

include interconversions via migration of a proton, such as keto-enol and imine-enamine isomerizations. Examples of proton tautomers are an imidazole moiety, wherein a proton can migrate between the two nitrogen atoms of the ring. Valence tautomers include interconversions by reorganization of some of the bonding electrons.

The present application also comprises the isotopically-labeled compounds of the present application which are identical to those recited herein, but one or more atoms are replaced by an atom having an atomic mass or mass number different from the atomic mass or mass number usually found in nature. Examples of isotopes that can be incorporated into the compounds of the present application include isotopes of hydrogen, carbon, nitrogen, oxygen, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{123}I$, $^{125}I$ and $^{36}Cl$, respectively.

Certain isotopically-labeled compounds of the present application (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Positron emitting isotopes such as $^{15}O$, $^{13}N$, $^{11}C$, and $^{18}F$ are useful for positron emission tomography (PET) studies to examine substrate occupancy, The isotopically labeled compounds of the present application can generally be prepared by following procedures analogous to those disclosed in the Schemes and/or in the Examples herein below, by substituting a non-isotopically labeled reagent with an isotopically labeled reagent.

Substitution with heavier isotopes (such as deuterium, i.e. $^{2}H$), may afford certain therapeutic advantages resulting from greater metabolic stability, for example, increased in vivo half-life or reduced dosage requirements, and hence may be preferred in some circumstances, wherein the deuterium substitution may be partial or complete, and partial deuterium substitution means that at least one hydrogen is substituted with at least one deuterium.

The compounds according to the present application may be asymmetric, e.g., having one or more stereoisomers. Unless otherwise stated, all stereoisomers are included, such as enantiomers and diastereoisomers. A compound according to the present application containing an asymmetric carbon atom may be isolated in a pure optically active form or a racemic form. A pure optically active form may be obtained by resolving a racemic mixture, or synthesized from a chiral starting material or a chiral reagent.

An important consideration factor in a synthesis route planning in the art is to select an appropriate protecting group for a reactive functional group, such as the amino group in the present application. For example, please refer to *Greene's Protective Groups in Organic Synthesis* (4th Ed). Hoboken, N.J.: John Wiley & Sons, Inc. All references cited in the present application are incorporated herein by reference in their entireties.

The present invention adopts the following abbreviation: Boc- represents t-butyloxycarbonyl.

EXAMPLES

The purpose of the following specific examples is to facilitate those skilled in the art to more clearly understand and implement the present invention. They should not be construed as limiting the scope of the present invention, but as merely exemplary illustrations and typical representatives of the present invention. It should be understood by those skilled in the art that the compounds according to the present invention may also be prepared by other synthetic routes. Non-limiting examples are provided below.

All operations involving easily oxidized or easily hydrolyzed raw materials are carried out under a nitrogen atmosphere. Unless otherwise indicated, the raw materials used in the present invention are commercially available and used directly without further purification.

Unless otherwise stated, all raw materials are commercially available and used directly without further purification. Column chromatography used in the present invention was performed using silica gel (200-300 mesh) from Qingdao Haiyang Chemical Co., Ltd. Thin layer chromatography was performed using prefabricated plates purchased from E. Merck Company (silica gel 60 PF254, 0.25 mm). Nuclear magnetic resonance (NMR) spectra were recorded on Varian VNMRS-400 nuclear magnetic resonance spectrometer with tetramethylsilane (TMS=δ 0.00) as the internal standard of chemical shifts. The NMR hydrogen spectrum data were recorded in the following format: proton number, peak pattern (s: singlet; d: doublet; t: triplet; q: quartet; m: multiplet), coupling constant (unit: Hz).

Intermediate 1: Synthesis of tert-butyl 4-(6-aminopyridin-3-yl)piperazine-1-carboxylate

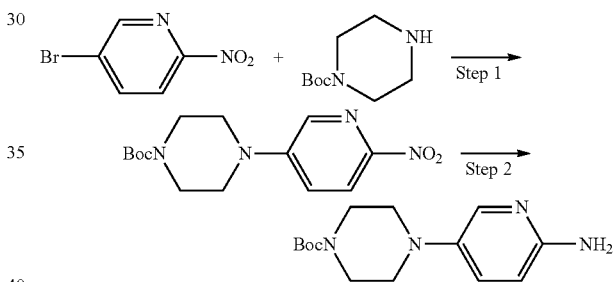

Step 1: Synthesis of tert-butyl 4-(6-nitropyridin-3-yl)piperazine-1-carboxylate

Tert-butyl piperazine-1-carboxylate (2.24 g, 12.0 mmol) and potassium carbonate (2.76 g, 20.0 mmol) were added to a solution of 5-bromo-2-nitropyridine (2.03 g, 10.0 mmol) in dimethyl sulfoxide (100 mL). The mixed solution was kept at 70° C. to react for 4 h, cooled, poured into water and filtered. The solid was washed with water, and dried to obtain tert-butyl 4-(6-nitropyridin-3-yl)piperazine-1-carboxylate (2.85 g, yield: 92.5%).

Step 2: Synthesis of tert-butyl 4-(6-aminopyridin-3-yl)piperazine-1-carboxylate

10% palladium/carbon catalyst (0.50 g) was added to a solution of tert-butyl 4-(6-nitropyridin-3-yl)piperazine-1-carboxylate (2.85 g, 9.24 mmoL) in methanol (150 mL). The mixed solution was stirred under a hydrogen atmosphere (1 atm) at room temperature for 24 h, and filtered through Celite. The filtrate was concentrated under reduced pressure to obtain tert-butyl 4-(6-aminopyridin-3-yl)piperazine-1-carboxylate (2.12 g, yield: 82.5%).

Intermediate 2: Synthesis of tert-butyl 6-amino-5',6'-dihydro-[3,4'-bipyridine]-1'(2'H)-carboxylate

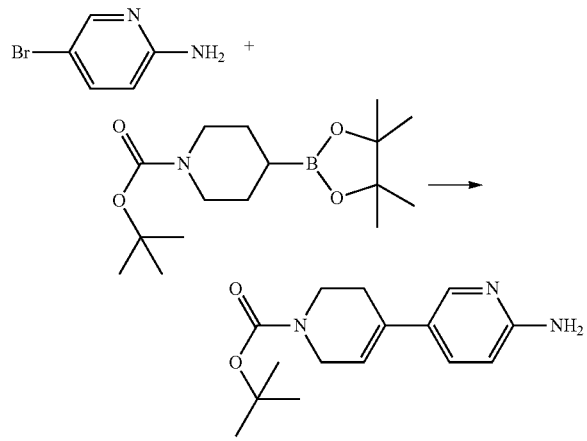

Tert-butyl 4-(4,4,5,5-tetramethyl-1,3,2-dioxaborolan-2-yl)-5,6-dihydropyridine-1(2H)-carboxylate (3.40 g, 0.011 mol) and sodium carbonate (2.12 g, 0.02 mmol) were successively added to a solution of 2-amino-5-bromopyridine (1.73 g, 0.01 mol) in 1,4-dioxane/water (100 mL, V/V=4:1). After nitrogen gas was introduced into the reaction system for 2 min, tetrakis(triphenylphosphine)palladium (0.58 g, 0.5 mmol) was added, and the resulting mixture was kept at 100° C. to react for 4 h. Water (50 mL) was added to the reaction mixture, and the resulting mixture was extracted with ethyl acetate (50 mL×2). The organic phase was dried with anhydrous sodium sulfate, filtered, and concentrated under reduced pressure. The residue was purified by column chromatography (petroleum ether:ethyl acetate=4:1) to obtain tert-butyl 6-amino-5',6'-dihydro-[3,4'-bipyridine]-1'(2'H)-carboxylate (2.53 g, yield: 92.0%).

$^1$H NMR (400 MHz, DMSO-$d_6$): 7.95 (1H, d, J=2.4 Hz), 7.47 (1H, dd, J=8.4 Hz, 2.4 Hz), 6.41 (1H, d, J=8.4 Hz), 6.98 (2H, s), 5.92 (1H, s), 3.93 (2H, s), 3.48 (2H, t, J=5.6 Hz), 2.36 (2H, t, J=5.6 Hz), 1.40 (9H, s).

Intermediate 3: Synthesis of tert-butyl 4-(6-aminopyridin-3-yl)piperidine-1-carboxylate

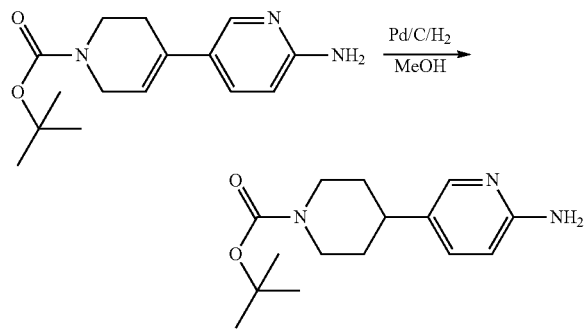

10% palladium/carbon catalyst (0.20 g) was added to a solution of tert-butyl 6-amino-5',6'-dihydro-[3,4'-bipyridine]-1'(2'H)-carboxylate (0.53 g, 1.92 mmoL) in methanol (50 mL). The mixed solution was stirred under a hydrogen atmosphere (1 atm) at room temperature for 2 h, and filtered through Celite. The filtrate was concentrated under reduced pressure to obtain tert-butyl 4-(6-aminopyridin-3-yl)piperidine-1-carboxylate (0.50 g, yield: 94.0%).

Intermediate 4: Synthesis of 5-(4-(dimethylamino)piperidin-1-yl)pyridin-2-amine

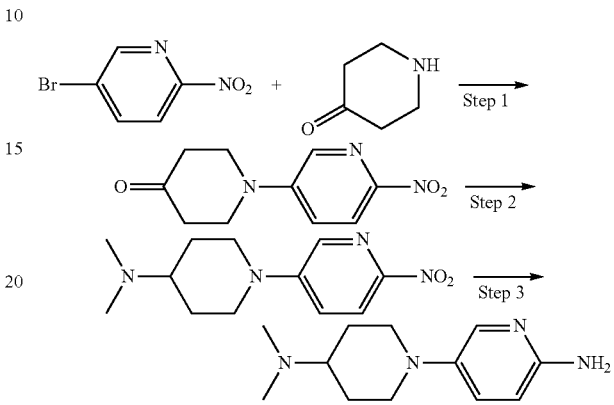

Step 1: Synthesis of 1-(6-nitropyridin-3-yl)piperidine-4-one

Piperidine-4-one (1.19 g, 12.0 mmol) and potassium carbonate (2.76 g, 20.0 mmol) were added to a solution of 5-bromo-2-nitropyridine (2.03 g, 10.0 mmol) in dimethyl sulfoxide (100 mL). The mixed solution was kept at 70° C. to react for 4 h, cooled, poured into water and filtered. The solid was washed with water, and dried to obtain 1-(6-nitropyridin-3-yl)piperidine-4-one (1.44 g, yield: 65.2%).

Step 2: Synthesis of N,N-dimethyl-1-(6-nitropyridin-3-yl)piperidin-4-amine

A tetrahydrofuran solution of dimethylamine (6.5 mL, 2.0 M) was added to a solution of 1-(6-nitropyridin-3-yl) piperidine-4-one (1.44 g, 6.51 mmoL) in 1,2-dichloroethane (100 mL). After the mixed solution was kept at room temperature to react for 0.5 h, sodium triacetoxyborohyride (2.76 g, 13.02 mmoL) was added, and the resulting mixture was further stirred at room temperature for 8 h. The reaction mixture was poured into water, and extracted with dichloromethane (100 mL×2). The organic phase was dried with anhydrous sodium sulfate, filtered, and concentrated under reduced pressure to obtain N,N-dimethyl-1-(6-nitropyridin-3-yl)piperidin-4-amine (1.32 g, 81.0%).

Step 3: Synthesis of 5-(4-(dimethylamino)piperidin-1-yl)pyridin-2-amine

10% palladium/carbon catalyst (0.50 g) was added to a solution of N,N-dimethyl-1-(6-nitropyridin-3-yl)piperidin-4-amine (1.32 g, 5.27 mmoL) in methanol (150 mL). The mixed solution was stirred under a hydrogen atmosphere (1 atm) at room temperature for 24 h, and filtered. The filtrate was concentrated under reduced pressure to obtain 5-(4-(dimethylamino)piperidin-1-yl)pyridin-2-amine (1.03 g, yield: 88.8%).

Intermediate 5: Synthesis of 6-bromo-2-chloro-7-cyclopentyl-7H-pyrrolo[2,3-d]pyrimidine

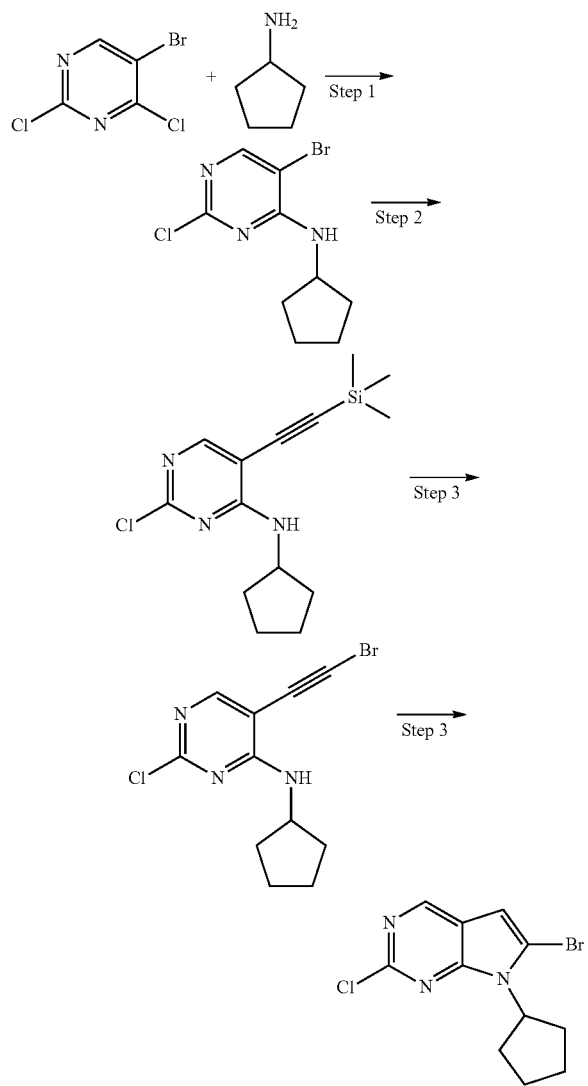

Step 1: Synthesis of 5-bromo-2-chloro-N-cyclopentylpyrimidin-4-amine

A solution of cyclopentylamine (9.4 g, 0.11 mol) in ethanol (100 mL) was slowly dropwise added to a solution of 5-bromo-2,6-dichloropyrimidine (22.8 g, 0.1 mol) and diisopropyl ethylamine (19.4 g, 0.15 mol) in ethanol (150 mL). After the dropwise addition was completed, the system was further stirred at room temperature for 2 h. The reaction mixture was concentrated under reduced pressure, water (250 mL) was added, and the resulting mixture was extracted with ethyl acetate (250 mL×2). The organic phase was dried with anhydrous sodium sulfate, filtered, and concentrated under reduced pressure. The residue was recrystallized with petroleum ether to obtain 5-bromo-2-chloro-N-cyclopentylpyrimidin-4-amine (23.5 g, yield: 84.8%).

Step 2: Synthesis of 2-chloro-N-cyclopentyl-5-((trimethylsilyl)ethynyl)pyrimidin-4-amine Triethylamine (15.2 g, 150.0 mmol), bis(triphenylphosphine)palladium dichloride (1.75 g, 2.5 mmol), cuprous iodide (1.9 g, 10.0 mmol) and trimethylsilylacetylene (7.4 g, 75.0 mmol) were added to a solution of 5-bromo-2-chloro-N-cyclopentylpyrimidin-4-amine (13.8 g, 50.0 mmol) in N-methylpyrrolidone (100 mL), and the reaction mixture was kept at 50° C. under the protection of nitrogen gas to react for 8 h. The reaction mixture was cooled, water (250 mL) was added thereto, and the resulting mixture was extracted with methyl tert-butyl ether (250 mL×2). The organic phase was dried with anhydrous sodium sulfate, filtered, and concentrated under reduced pressure. The residue was purified by column chromatography (petroleum ether:ethyl acetate=10:1) to obtain 2-chloro-N-cyclopentyl-5-((trimethylsilyl)ethynyl)pyrimidin-4-amine (7.8 g, yield: 53.1%).

$^1$H NMR (400 MHz, CDCl$_3$): 8.19 (1H, s), 5.48 (1H, d, J=7.6 Hz), 4.49-4.58 (1H, m), 2.10-2.15 (2H, m), 1.66-1.78 (4H, m), 1.42-1.52 (2H, m), 0.29 (9H, s).

Step 3: Synthesis of 2-chloro-5-bromoethynyl-N-cyclopentylpyrimidin-4-amine

Silver nitrate (5.4 g, 31.8 mmol) and N-bromosuccinimide (5.7 g, 31.8 mmol) were successively added to a solution of 2-chloro-N-cyclopentyl-5-((trimethylsilyl)ethynyl)pyrimidin-4-amine (7.8 g, 26.5 mmol) in tetrahydrofuran (150 mL), and the resulting mixture was kept at room temperature to react for 2 h. Water (150 mL) was added to the reaction mixture, and the resulting mixture was extracted with ethyl acetate (150 mL×2). The organic phase was dried with anhydrous sodium sulfate, filtered, and concentrated under reduced pressure. The residue was purified by column chromatography (petroleum ether:ethyl acetate=10:1) to obtain 2-chloro-5-bromoethynyl-N-cyclopentylpyrimidin-4-amine (6.1 g, yield: 76.3%).

Step 4: Synthesis of 6-bromo-2-chloro-7-cyclopentyl-7H-pyrrolo[2,3-d]pyrimidine Tetrabutylammonium fluoride trihydrate (16.0 g, 50.8 mmol) was added to a solution of 2-chloro-5-bromoethynyl-N-cyclopentylpyrimidin-4-amine (6.1 g, 20.3 mmol) in tetrahydrofuran (150 mL), and the resulting mixture was kept at room temperature to react for 2 h. Water (150 mL) was added to the reaction mixture, and the resulting mixture was extracted with ethyl acetate (150 mL×2). The organic phase was dried with anhydrous sodium sulfate, filtered, and concentrated under reduced pressure. The residue was purified by column chromatography (petroleum ether:ethyl acetate=5:1) to obtain 6-bromo-2-chloro-7-cyclopentyl-7H-pyrrolo[2,3-d]pyrimidine (5.2 g, yield: 85.2%).

$^1$H NMR (400 MHz, CDCl$_3$): 8.69 (1H, s), 6.64 (1H, s), 5.10-5.19 (1H, m), 2.35-2.44 (2H, m), 2.03-2.15 (4H, m), 1.68-1.78 (2H, m).

Intermediate 6: Synthesis of 2-chloro-7-cyclopentyl-N,N-dimethyl-7H-pyrrolo[2,3-d]pyrimidine-6-carboxamide

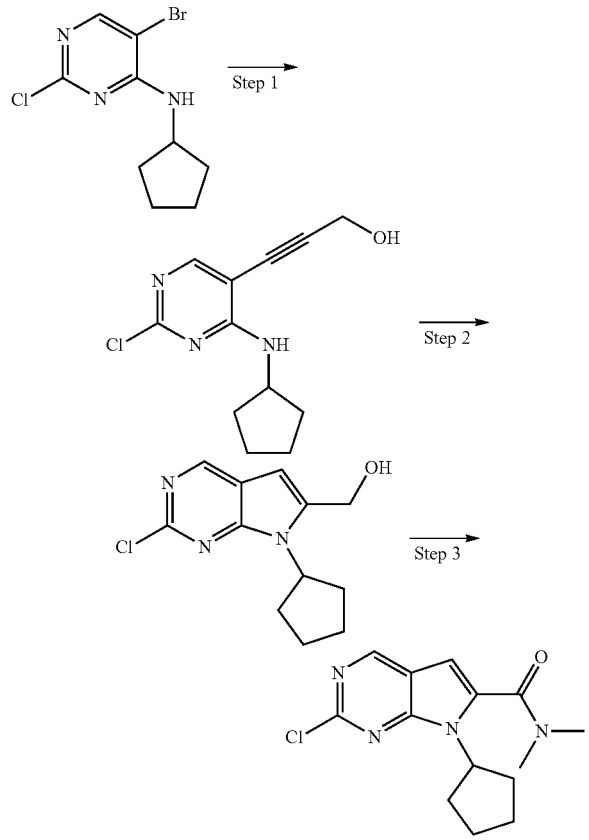

Step 1: 3-(2-chloro-4-(cyclopentylamino)pyrimidin-5-yl)prop-2-yn-1-ol

Tetrabutylammonium fluoride trihydrate (28.5 g, 90.5 mmol), [1,1'-bis(diphenylphosphino)ferrocene]palladium dichloride dichloromethane complex (1.3 g, 1.81 mmol) and propynol (4.1 g, 72.4 mmol) were added to a solution of 5-bromo-2-chloro-N-cyclopentylpyrimidin-4-amine (10.0 g, 36.2 mmol) in tetrahydrofuran (150 mL). The mixed solution was kept at 70° C. to react for 5 h. The reaction mixture was cooled, water (500 mL) was added thereto, and the resulting mixture was extracted with ethyl acetate (250 mL×2). The organic phase was dried with anhydrous sodium sulfate, filtered, and concentrated under reduced pressure. The residue was purified by column chromatography (petroleum ether:ethyl acetate=10:1) to obtain 3-(2-chloro-4-(cyclopentylamino)pyrimidin-5-yl)prop-2-yn-1-ol (6.0 g, yield: 65.9%).

$^1$H NMR (400 MHz, CDCl$_3$): 8.07 (1H, s), 5.56 (1H, d, J=7.2 Hz), 4.54 (2H, s), 4.38-4.47 (1H, m), 2.22-2.34 (1H, brs), 2.09-2.17 (2H, m), 1.62-1.77 (4H, m), 1.41-1.50 (2H, m).

Step 2: (2-chloro-7-cyclopentyl-7H-pyrrolo[2,3-d]pyrimidin-6-yl)methanol

Tetrabutylammonium fluoride trihydrate (18.8 g, 59.6 mmol) was added to a solution of 3-(2-chloro-4-(cyclopentylamino)pyrimidin-5-yl)prop-2-yn-1-ol (6.0 g, 23.8 mmol) in tetrahydrofuran (150 mL). The mixed solution was kept at 70° C. to react for 12 h. The reaction mixture was cooled, water (150 mL) was added thereto, and the resulting mixture was extracted with ethyl acetate (150 mL×2). The organic phase was dried with anhydrous sodium sulfate, filtered, and concentrated under reduced pressure. The residue was purified by column chromatography (petroleum ether:ethyl acetate=10:1) to obtain (2-chloro-7-cyclopentyl-7H-pyrrolo[2,3-d]pyrimidin-6-yl)methanol (4.89 g, yield: 81.5%).

$^1$H NMR (400 MHz, CDCl$_3$): 8.65 (1H, s), 6.43 (1H, s), 4.87-4.95 (1H, m), 4.82 (2H, s), 2.35-2.43 (2H, m), 1.99-2.19 (6H, m).

Step 3: Synthesis of 2-chloro-7-cyclopentyl-N,N-dimethyl-7H-pyrrolo[2,3-d]pyrimidine-6-carboxamide A tetrahydrofuran solution of dimethylamine (15.8 mL, 2.0 M) and sodium cyanide (0.39 g, 7.9 mmol) were added to a solution of (2-chloro-7-cyclopentyl-7H-pyrrolo[2,3-d]pyrimidin-6-yl)methanol (2.0 g, 7.9 mmol) in N,N-dimethylformamide (15 mL). The mixed solution was stirred at room temperature to react for 4 min. Active manganese dioxide (30.9 g, 355.5 mmoL) was added in batches to the reaction mixture. The reaction mixture was further stirred at room temperature for 12 h, and filtered. The filtrate was poured into water (100 mL), and extracted with ethyl acetate (100 mL×2). The organic phase was dried with anhydrous sodium sulfate, filtered, and concentrated under reduced pressure. The residue was purified by column chromatography (petroleum ether:ethyl acetate=4:1) to obtain 2-chloro-7-cyclopentyl-N,N-dimethyl-7H-pyrrolo[2,3-d]pyrimidine-6-carboxamide (1.75 g, yield: 75.1%).

$^1$H NMR (400 MHz, DMSO-d$_6$): 8.95 (1H, s), 6.78 (1H, s), 4.78 (1H, quiv, J=8.8 Hz), 3.03 (3H, s), 2.99 (3H, s), 2.16-2.26 (2H, m), 1.87-2.02 (4H, m), 1.56-1.66 (2H, m).

Example 1: Synthesis of 7-cyclopentyl-6-methylsulfonyl-N-(5-(piperazin-1-yl)pyridin-2-yl)-7H-pyrrolo[2,3-d]pyrimidin-2-amine hydrochloride

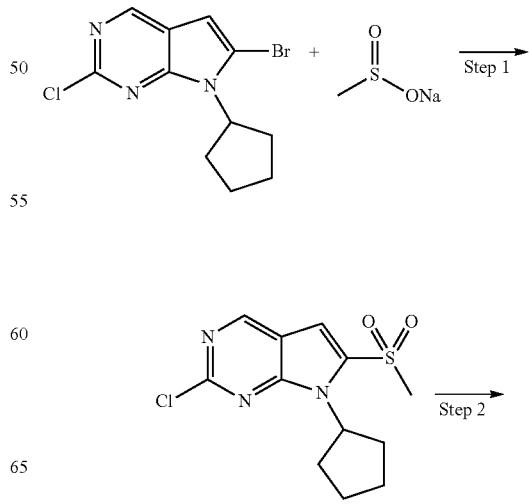

-continued

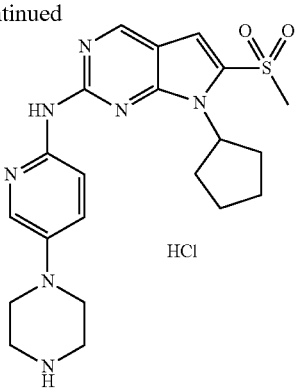

Step 1: Synthesis of 6-methylsulfonyl-2-chloro-7-cyclopentyl-7H-pyrrolo[2,3-d]pyrimidine Cuprous iodide (48.6 mg, 0.25 mmol) and sodium methanesulfinate (61.3 mg, 0.6 mmol) were successively added to a solution of 6-bromo-2-chloro-7-cyclopentyl-7H-pyrrolo[2,3-d]pyrimidine (150 mg, 0.5 mmol) in dimethyl sulfoxide (50 mL), and the resulting mixture was kept at 80° C. to react for 48 h. Water (50 mL) was added to the reaction mixture, and the resulting mixture was extracted with ethyl acetate (50 mL×2). The organic phase was dried with anhydrous sodium sulfate, filtered, and concentrated under reduced pressure. The residue was purified by column chromatography (petroleum ether:ethyl acetate=4:1) to obtain 6-methylsulfonyl-2-chloro-7-cyclopentyl-7H-pyrrolo[2,3-d]pyrimidine (65.2 mg, yield: 43.5%).

$^1$H NMR (400 MHz, CDCl$_3$): 8.97 (1H, s), 7.30 (1H, s), 5.25-5.34 (1H, m), 3.25 (3H, s), 2.48-2.57 (2H, m), 2.10-2.24 (4H, m), 1.71-1.79 (2H, m).

Step 2: Synthesis of 7-cyclopentyl-6-methylsulfonyl-N-(5-(piperazin-1-yl)pyridin-2-yl)-7H-pyrrolo[2,3-d]pyrimidin-2-amine hydrochloride 5-(4-Tert-butoxycarbonyl)piperazin-2-aminopyridine (i.e., Intermediate 1: tert-butyl 4-(6-aminopyridin-3-yl)piperazine-1-carboxylate, 83.5 mg, 0.3 mmol), tris(dibenzylideneacetone)dipalladium (9.2 mg, 0.01 mmol), binaphthyl diphenyl phosphate (12.5 mg, 0.02 mmol), and cesium carbonate (195.5 mg, 0.6 mmol) were successively added to a solution of 6-methylsulfonyl-2-chloro-7-cyclopentyl-7H-pyrrolo[2,3-d]pyrimidine (65.2 mg, 0.2 mmol) in methylbenzene (50 mL), and the resulting mixture was kept at 110° C. to react for 4 h. Water (50 mL) was added to the reaction mixture, and the resulting mixture was extracted with ethyl acetate (50 mL×2). The organic phase was dried with anhydrous sodium sulfate, filtered, and concentrated under reduced pressure. The residue was purified by column chromatography (petroleum ether:ethyl acetate=2:1) to obtain 7-cyclopentyl-6-methylsulfonyl-N-(5-(4-tert-butoxycarbonylpiperazin-1-yl)pyridin-2-yl)-7H-pyrrolo[2,3-d]pyrimidin-2-amine.

7-Cyclopentyl-6-methylsulfonyl-N-(5-(4-tert-butoxycarbonylpiperazin-1-yl)pyridin-2-yl)-7H-pyrrolo[2,3-d]pyrimidin-2-amine was dissolved in 50 mL of a methanol solution of hydrogen chloride (4.0 mol/L), and the resulting mixture was stirred at room temperature for 2 h, and concentrated to obtain 7-cyclopentyl-6-methylsulfonyl-N-(5-(piperazin-1-yl)pyridin-2-yl)-7H-pyrrolo[2,3-d]pyrimidin-2-amine hydrochloride (80.5 mg, yield: 77%).

$^1$H NMR (400 MHz, DMSO-d$_6$): 10.87-11.04 (1H, brs), 9.20-9.31 (2H, brs), 9.10 (1H, s), 7.95-7.99 (2H, m), 7.86 (1H, d, J=9.2 Hz), 7.32 (1H, s), 5.12-5.21 (1H, m), 3.46 (3H, s), 3.39-3.42 (4H, m), 3.20-3.29 (4H, m), 2.42-2.48 (2H, m), 2.01-2.09 (4H, m), 1.63-1.75 (2H, m).

Example 2: Synthesis of 7-cyclopentyl-6-ethylsulfonyl-N-(5-(piperazin-1-yl)pyridin-2-yl)-7H-pyrrolo[2,3-d]pyrimidin-2-amine hydrochloride

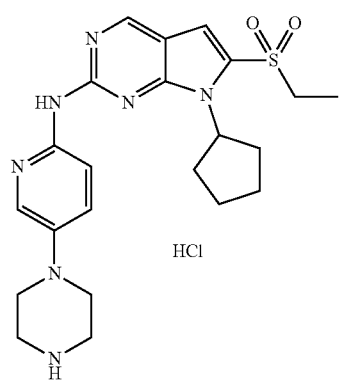 [SMILES: CCS(=O)(=O)c1cc2cnc(Nc3ccc(N4CCNCC4)cn3)nc2n1C1CCCC1 ; Cl]

The title compound was synthesized according to the method of Example 1 except that sodium methanesulfinate was replaced with sodium ethanesulfinate.

$^1$H NMR (400 MHz, DMSO-d$_6$): 11.43 (1H, s), 9.65 (2H, s), 9.15 (1H, s), 7.86-8.12 (3H, m), 7.37 (1H, s), 5.08-5.13 (1H, m), 3.39-3.56 (6H, m), 3.16-3.31 (4H, m), 2.38-2.48 (2H, m), 1.97-2.14 (4H, m), 1.59-1.74 (2H, m), 1.19 (3H, t, J=7.2 Hz).

Example 3: Synthesis of 7-cyclopentyl-6-methylsulfonyl-N-(5-(4-(dimethylamino) piperidin-1-yl)pyridin-2-yl)-7H-pyrrolo[2,3-d]pyrimidin-2-amine hydrochloride

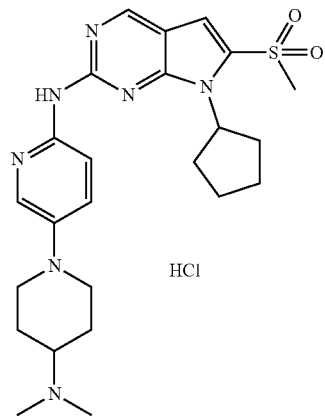 [SMILES: CN(C)C1CCN(c2ccc(Nc3ncc4cc(S(C)(=O)=O)n(C5CCCC5)c4n3)nc2)CC1 ; Cl]

The title compound was synthesized according to the method of Example 1 except that 5-(4-tert-butoxycarbonyl)piperazin-2-aminopyridine was replaced with Intermediate 4.

¹H NMR (400 MHz, DMSO-d₆): 11.39-11.48 (1H, brs), 11.09-11.39 (1H, brs), 9.11 (1H, s), 8.01-8.11 (2H, m), 7.91 (1H, d, J=9.2 Hz), 7.32 (1H, s), 5.15 (1H, quiv, J=8.0 Hz), 3.81-3.85 (2H, m), 3.47 (3H, s), 3.26-3.46 (1H, m), 2.72-2.79 (2H, m), 2.69 (3H, s), 2.67 (3H, s), 2.40-2.44 (2H, m), 2.15-2.18 (2H, m), 2.02-2.10 (4H, m), 1.73-1.84 (2H, m), 1.62-1.72 (2H, m).

Example 4: Synthesis of 7-cyclopentyl-6-methylsulfonyl-N-(5-(1,2,3,6-4H-pyridin-4-yl)pyridin-2-yl)-7H-pyrrolo[2,3-d]pyrimidin-2-amine hydrochloride

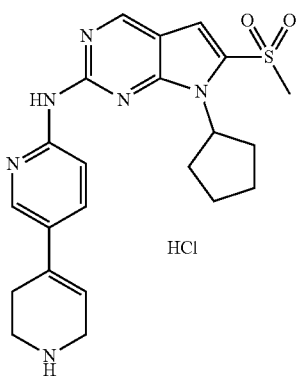 [SMILES: CS(=O)(=O)c1cc2cnc(Nc3ccc(C4=CCNCC4)cn3)nc2n1C1CCCC1 ; Cl]

The title compound was synthesized according to the method of Example 1 except that 5-(4-tert-butoxycarbonyl)piperazin-2-aminopyridine was replaced with Intermediate 2.

¹H NMR (400 MHz, DMSO-d₆): 11.02-11.19 (1H, brs), 9.20-9.27 (2H, brs), 9.13 (1H, s), 8.43 (1H, d, J=1.6 Hz), 8.22 (1H, dd, J=9.6 Hz, 1.6 Hz), 8.01 (1H, d, J=9.6 Hz), 7.33 (1H, s), 6.34 (1H, s), 5.16-5.22 (1H, m), 3.74-3.80 (2H, m), 3.47 (3H, s), 3.30-3.34 (2H, m), 2.68-2.74 (2H, m), 2.45-2.52 (2H, m), 2.04-2.14 (4H, m), 1.67-1.76 (2H, m).

Example 5: Synthesis of 7-cyclopentyl-6-methylsulfonyl-N-(5-(piperidin-4-yl)pyridin-2-yl)-7H-pyrrolo[2,3-d]pyrimidin-2-amine hydrochloride

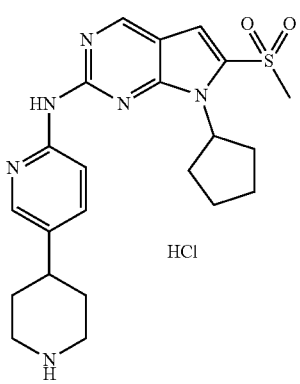 [SMILES: CS(=O)(=O)c1cc2cnc(Nc3ccc(C4CCNCC4)cn3)nc2n1C1CCCC1 ; Cl]

The title compound was synthesized according to the method of Example 1 except that 5-(4-tert-butoxycarbonyl)piperazin-2-aminopyridine was replaced with Intermediate 3.

¹H NMR (400 MHz, DMSO-d₆): 11.46-11.63 (1H, brs), 9.17 (1H, s), 9.15 (2H, s), 8.27 (1H, d, J=1.6 Hz), 8.10 (1H, dd, J=8.8 Hz, 1.6 Hz), 7.88 (1H, d, J=8.8 Hz), 7.37 (1H, s), 5.14-5.22 (1H, m), 3.49 (3H, s), 3.35-3.38 (2H, m), 2.95-3.01 (3H, m), 2.42-2.48 (2H, m), 2.04-2.16 (4H, m), 1.85-1.19 (4H, m), 1.61-1.74 (2H, m).

Example 6: Synthesis of 7-cyclopentyl-6-N,N-dimethylcarbamoyl-N-(5-(1,2,3,6-4H-pyridin-4-yl)pyridin-2-yl)-7H-pyrrolo[2,3-d]pyrimidin-2-amine hydrochloride

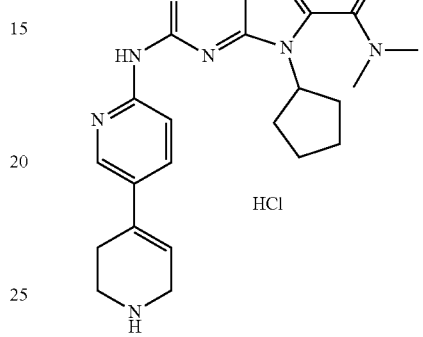

The title compound was synthesized according to the method in Step 2 of Example 1 using Intermediates 2 and 6 as starting materials.

¹H NMR (400 MHz, DMSO-d₆): 11.93-12.04 (1H, brs), 9.61 (2H, s), 9.07 (1H, s), 8.44 (1H, d, J=2.0 Hz), 8.37 (1H, dd, J=8.8 Hz, 2.0 Hz), 7.68 (1H, d, J=8.8 Hz), 6.87 (1H, s), 6.37 (1H, s), 4.76-4.83 (1H, m), 3.72-3.79 (2H, m), 3.25-3.35 (2H, m), 3.04 (6H, s), 2.66-2.74 (2H, m), 2.23-2.36 (2H, m), 1.93-2.08 (4H, m), 1.59-1.72 (2H, m).

Example 7: Synthesis of 7-cyclopentyl-6-phenylsulfonyl-N-(5-(piperazin-1-yl)pyridin-2-yl)-7H-pyrrolo[2,3-d]pyrimidin-2-amine hydrochloride

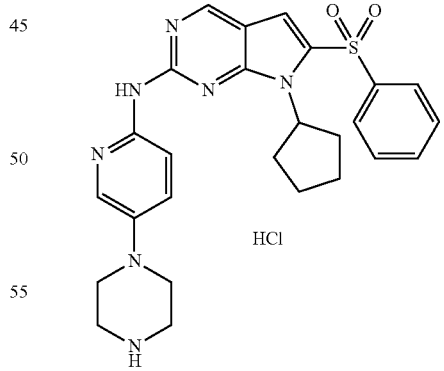

The title compound was synthesized according to the method of Example 1 except that sodium methanesulfinate was replaced with sodium benzenesulfinate.

¹H NMR (400 MHz, DMSO-d₆): 11.26-11.41 (1H, brs), 9.59 (2H, s), 9.16 (1H, s), 7.97-8.08 (4H, m), 7.77-7.82 (2H, m), 7.67-7.74 (2H, m), 7.52 (1H, s), 4.95-5.02 (1H, m), 3.37-3.48 (4H, m), 3.15-3.22 (4H, m), 2.15-2.28 (2H, m), 1.89-2.01 (2H, m), 1.44-1.62 (4H, m).

Comparative Example 1: Synthesis of 7-cyclopentyl-2-(5-(piperazin-1-yl-pyridin-2-ylamino)-7H-pyrrolo[2,3-d]pyrimidine-6-carboxylic acid dimethylamide (ribociclib) hydrochloride

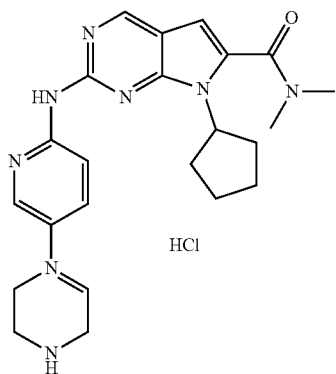

Ribociclib (100.0 mg, 0.23 mmol) was dissolved in 50 mL of a methanol solution of hydrogen chloride (4.0 mol/L), and the resulting mixture was stirred at room temperature for 2 h and concentrated to obtain ribociclib hydrochloride (108.4 mg, yield: 100.0%).

$^1$H NMR (400 MHz, DMSO-$d_6$): 11.68 (1H, s), 9.68 (2H, s), 9.04 (1H, s), 8.12 (1H, dd, J=9.2 Hz, 2.8 Hz), 7.99 (1H, d, J=2.8 Hz), 7.65 (1H, d, J=9.2 Hz), 6.85 (1H, s), 4.77-4.86 (1H, m), 3.44-3.47 (4H, m), 3.21-3.30 (4H, m), 3.06 (3H, s), 2.51 (3H, s), 2.27-2.42 (2H, m), 1.93-2.09 (4H, m), 1.58-1.72 (2H, m).

Biological Evaluation

Test Example 1: Assay of Inhibiting Effect of the Compounds of the Present Invention on Kinase Activity of CDK4/CDK6

A method for in vitro kinase activity inhibition assay of CDK4/CyclinD3 and CDK6/CyclinD3 is established as follows:

LANCE method of PerkinElmer Inc. was used in the assay, and recombinant CDK4/CyclinD3 (Item No.: 04-105) and CDK6/CyclinD3 (Item No.: 04-107) kinases were purchased from Cama Biosciences, Inc. Substrate ULight-MBP (Item No.: TRF0109) and Eu-labeled anti-MBP antibody (Item No.: TRF0201) were purchased from PerkinElmer. HEPES PH7.5 (Item No.: #15630080), DTT (Item No.: #D1532), $MgCl_2$ (Item No.: # AM9530G), EGTA (Item No.: # E1219), and EDTA (Item No.: # AM9260G) were purchased from Life Technology. Firstly, a 1× buffer solution A (50 mM HEPES, PH 7.5, 10 mM $MgCl_2$, 1 mM EGTA, 0.01% Tween 20 and 2 mM DTT) was prepared. A compound to be tested was dissolved in DMSO to 1 mM, serially diluted with DMSO, and then diluted 25-fold with the buffer solution A (final concentration of DMSO: 1%). CDK4/CyclinD3 and CDK6/CyclinD3 were diluted respectively with the buffer solution A. Finally, the buffer solution A was used to prepare the substrate and ATP. 4 μl of CDK4/CyclinD3 (final concentration: 2 nM) or CDK6/CyclinD3 (final concentration: 4 nM), 2 μl of the diluted compound, and 4 μl of a mixture of the substrate (final concentration: 50 nM) and ATP (final concentration: 200 μM) were added to reaction wells, and the resulting mixture was kept at room temperature to react for 1 h. Then, an EDTA solution was added to terminate the reaction, and Eu-labeled anti-MBP antibody was added and the resulting mixture was incubated at room temperature for additional 1 h. EnVision was used to read fluorescent signals (excitation wavelength: 320 nM, emission wavelength: 615 nM and 650 nM). The results are shown in Table 1.

TABLE 1

$IC_{50}$ of the Compounds of the Present Invention for Inhibiting CDK Kinase (CDK4, CDK6) Activity

| Compounds | $IC_{50}$(CDK4)/nM | $IC_{50}$(CDK6)/nM |
|---|---|---|
| Comparative Example 1 | 2.14 | 26.95 |
| Example 1 | 0.80 | 5.70 |
| Example 2 | 2.12 | 21.04 |
| Example 3 | 3.40 | 18.68 |
| Example 4 | 2.57 | 11.06 |
| Example 5 | 1.46 | 9.85 |
| Example 6 | 2.37 | 30.62 |

Conclusion: The compounds of the present invention have a significant inhibiting effect on CDK kinase (CDK4, CDK6) activity.

Test Example 2: Assay of Inhibiting Effect of the Compounds on Proliferation of Human Colon Cancer Cell Line Colo-205 and Breast Cancer Cell Line MCF7

Colo-205 (Crown Bioscience Inc.) and MCF7 (Beijing Jinzijing Biology Medicine Technology Co., Ltd.) cells were inoculated into a 96-well plate (Corning, Item No.: 3599) at a density of 1000 cells/well, and incubated overnight. A compound at different concentrations (10000 nM, 3000 nM, 1000 nM, 300 nM, 100 nM, 30 nM, 10 nM, 3 nM, 1 nM, 0.3 nM, 0 nM, final concentration of DMSO: 0.1%) was added on the next day, and the incubation was continued for additional 72 hours. The culture medium was sucked with a vacuum pump, 50 ul of Cell-Titer Glo reagent (Promega, Item No.: G7572) was added to each well, and shaken for 10 min. Chemiluminescent signals were collected by EnVision® Multilabel Reader (PerkinElmer Inc.) to detect the cell viability and calculate the half maximal inhibitory concentration of the compound for inhibiting cell proliferation. The results are shown in Table 2 and Table 3.

TABLE 2

$IC_{50}$ of the Compounds of the Present Invention for Inhibiting Proliferation of Colo205 Cell

| Compounds | $IC_{50}$(Colo205)/nM |
|---|---|
| Comparative Example 1 | 2691 |
| Example 1 | 270.8 |
| Example 4 | 311.6 |
| Example 5 | 470.3 |
| Example 6 | 1255 |

Conclusion: The compounds of the present invention have a significant inhibiting effect on the proliferation of Colo205 Cell.

TABLE 3

IC$_{50}$ of the Compounds of the Present Invention
for Inhibiting Proliferation of MCF7 Cell

| Compounds | IC$_{50}$(MCF7)/nM |
| --- | --- |
| Comparative Example 1 | 325.7 |
| Example 1 | 114.4 |
| Example 4 | 175.3 |
| Example 6 | 333.0 |

Conclusion: The compounds of the present invention have a significant inhibiting effect on the proliferation of MCF-7 Cell.

Pharmacokinetics Evaluation

3 Healthy adult male rats were used for each tested compound. The tested compound was suspended in 20% sulfobutyl ether-β-cyclodextrin at a concentration of 1 mg/mL, and then was intragastrically administered at a single dose of 5 mg/kg (administered volume: 5 mL/kg). The animals to be intragastrically administered were fasted overnight prior to the experiment, i.e., fasted from 10 h prior to the administration to 4 h after the administration, and blood samples were collected in 0.25, 0.5, 1, 2, 4, 6, 8 and 24 h after the intragastric administration. About 0.3 mL of whole blood was collected from the orbital venous plexus, and put in a heparin anticoagulant tube. The sample was centrifuged at 4° C. at 4000 rpm for 5 min. The plasma was transferred to a centrifuge tube, and kept at −80° C. until analysis. Concentration of the tested compound in the plasma sample was analyzed using non-validated liquid chromatography-tandem mass spectrometry (LC-MS/MS). Plasma concentration-time data of individual animals were analyzed using WinNonlin (Professional Edition, Version 6.3; Pharsight Corporation) software. A non-compartment model was used for concentration analysis. Pharmacokinetic parameters of the tested compound were calculated, and the results are shown in Table 4.

TABLE 4

Pharmacokinetic Parameters of the
Compounds of the Present Invention

| Kinetic Parameters | Comparative Example 1 | Example 1 | Example 4 | Example 6 |
| --- | --- | --- | --- | --- |
| T$_{1/2}$ (hr) | 4.25 | 7.23 | 3.28 | 3.76 |
| T$_{max}$ (hr) | 2.67 | 1.33 | 3.0 | 3.33 |
| C$_{max}$ (ng/mL) | 15.8 | 255 | 90.0 | 74.3 |
| AUC$_{0\text{-}inf}$ (hr*ng/mL) | 120 | 1961 | 889 | 627 |

Conclusion: The results show that the compounds of the present invention have good pharmacokinetic absorption and significantly better oral absorption effects in the rats compared with Comparative Example 1.

What is claimed is:

1. A compound of Formula III or a pharmaceutically acceptable salt or solvate thereof,

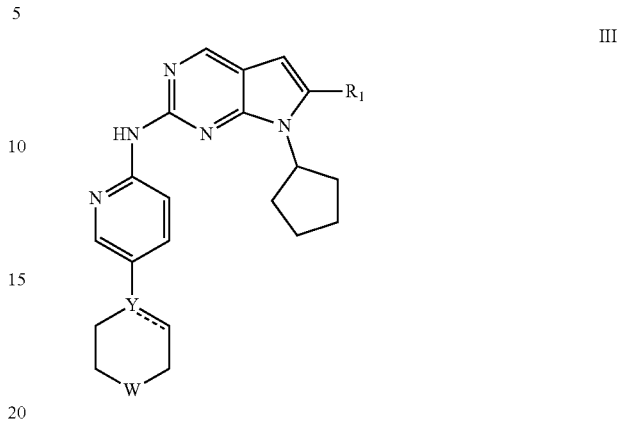

wherein

R$_1$ is selected from the group consisting of —S(O)$_2$R$_4$ and —C(O)NR$_5$R$_6$;

R$_4$ is selected from the group consisting of hydrogen, C$_{1\text{-}6}$ alkyl, C$_{2\text{-}6}$ alkenyl, C$_{2\text{-}6}$ alkynyl, C$_{3\text{-}6}$ cycloalkyl, 3- to 6-membered heterocycloalkyl, 5- to 10-membered aryl, and 5- to 10-membered heteroaryl, which are optionally substituted by one or more R$_a$;

R$_5$ and R$_6$ are independently selected from the group consisting of hydrogen, C$_{1\text{-}6}$ alkyl, C$_{2\text{-}6}$ alkenyl, C$_{2\text{-}6}$ alkynyl, C$_{3\text{-}6}$ cycloalkyl, 3- to 6-membered heterocycloalkyl, 5- to 10-membered aryl, and 5- to 10-membered heteroaryl, which are optionally substituted by one or more R$_a$;

the group

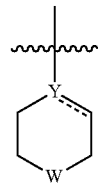

is

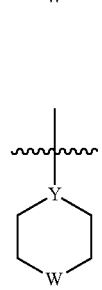

when the group

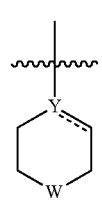

is

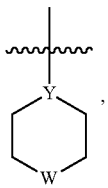

Y is selected from the group consisting of CH and N; and when the group

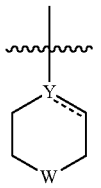

is

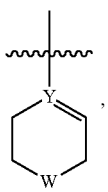

Y is C;
W is selected from the group consisting of O, S, CR₇R₈ and NR₉;
R₇ and R₈ are independently selected from the group consisting of hydrogen, —NR₁₀R₁₁, C₁₋₆ alkyl, C₃₋₆ cycloalkyl, 5- to 10-membered aryl, and 5- to 10-membered heteroaryl, which are optionally substituted by one or more Rₐ;
R₁₀ and R₁₁ are independently selected from the group consisting of hydrogen, C₁₋₆ alkyl, C₃₋₆ cycloalkyl, 5- to 10-membered aryl, and 5- to 10-membered heteroaryl, which are optionally substituted by one or more Rₐ;
R₉ is selected from the group consisting of hydrogen, C₁₋₆ alkyl, C₃₋₆ cycloalkyl, 5- to 10-membered aryl, and 5- to 10-membered heteroaryl, which are optionally substituted by one or more Rₐ;
Rₐ is selected from the group consisting of halogen, cyano, —R, —OR, =O, —SR, —NR₂, =NR, —C(halogen)₃, —CR(halogen)₂, —CR₂(halogen), —OCN, —SCN, —N=C=O, —NCS, —NO, —NO₂, —NRC(=O)R, —NRC(=O)OR, —NRC(=O)NRR, —C(=O)NRR, —C(=O)OR, —OC(=O)NRR, —OC(=O)OR, —C(=O)R, —S(=O)₂OR, —S(=O)₂R, —OS(=O)₂OR, —S(=O)₂NRR, —S(=O)R, —NRS(=O)₂R, —NRS(=O)₂NRR, —NRS(=O)₂OR, —OP(=O)(OR)₂, —P(=O)(OR)₂, —C(=O)R, —C(=S)R, —C(=O)OR, —C(=S)OR, —C(=O)SR, —C(=S)SR, —C(=O)NRR, —C(=S)NRR, —C(=NR)NRR and —NRC(=NR)NRR; and
R is independently selected from the group consisting of hydrogen, C₁₋₆ alkyl, C₃₋₆ cycloalkyl, 3- to 6-membered heterocycloalkyl, 5- to 10-membered aryl and 5- to 10-membered heteroaryl, wherein when Rₐ is —R, R is not hydrogen; and
provided that: when R₁ is selected from —C(O)NR₅R₆, the group

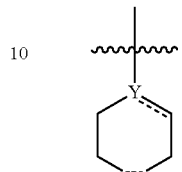

is

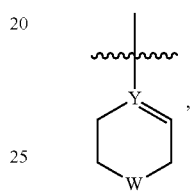

and Y is C.

2. The compound or a pharmaceutically acceptable salt or solvate thereof according to claim 1, wherein W is selected from the group consisting of CR₇R₈ and NR₉.

3. The compound or a pharmaceutically acceptable salt or solvate thereof according to claim 2, wherein R₄ is selected from the group consisting of C₁₋₆ alkyl and phenyl, which are optionally substituted by one or more Rₐ.

4. The compound or a pharmaceutically acceptable salt or solvate thereof according to claim 2, wherein R₅ and R₆ are independently selected from C₁₋₆ alkyl, which is optionally substituted by one or more Rₐ.

5. The compound or a pharmaceutically acceptable salt or solvate thereof according to claim 2, wherein the group

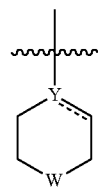

is

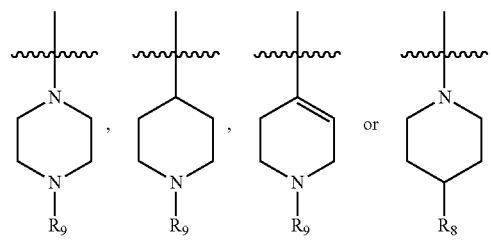

6. The compound or a pharmaceutically acceptable salt or solvate thereof according to claim 1, wherein R₇ is hydrogen, and R₈ is selected from the group consisting of hydrogen, —NR₁₀R₁₁, C₁₋₆ alkyl and C₃₋₆ cycloalkyl, which are optionally substituted by one or more R_a.

7. The compound or a pharmaceutically acceptable salt or solvate thereof according to claim 1, wherein R₉ is selected from the group consisting of hydrogen and C₁₋₄ alkyl, which are optionally substituted by one or more R_a.

8. The compound or a pharmaceutically acceptable salt or solvate thereof according to claim 1, wherein R₁₀ and R₁₁ are independently selected from the group consisting of hydrogen, C₁₋₆ alkyl and C₃₋₆ cycloalkyl, which are optionally substituted by one or more R_a.

9. The compound or a pharmaceutically acceptable salt or solvate thereof according to claim 5, wherein the group

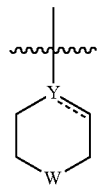

is

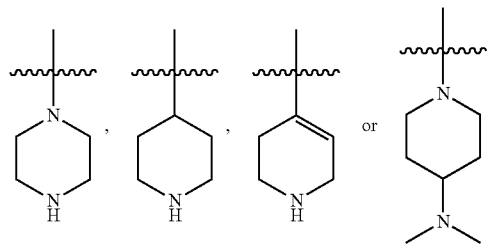

10. The compound or a pharmaceutically acceptable salt or solvate thereof according to claim 1, wherein the compound of Formula III is a compound of Formula IV,

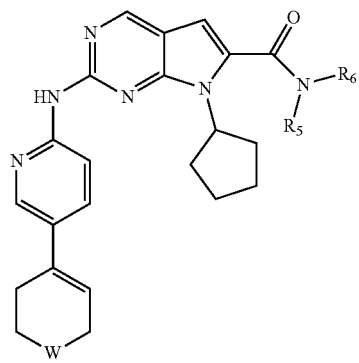

IV wherein

W is selected from the group consisting of CR₇R₈ and NR₉; and

R₅, R₆, R₇, R₈ and R₉ are as defined in claim 1.

11. The compound or a pharmaceutically acceptable salt or solvate thereof according to claim 10, wherein the group

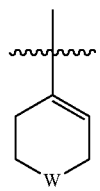

is

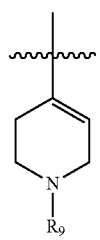

12. The compound or a pharmaceutically acceptable salt or solvate thereof according to claim 1, wherein the compound of Formula III is a compound selected from the group consisting of:

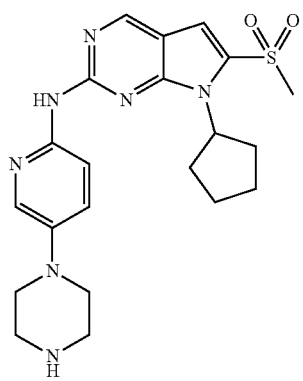

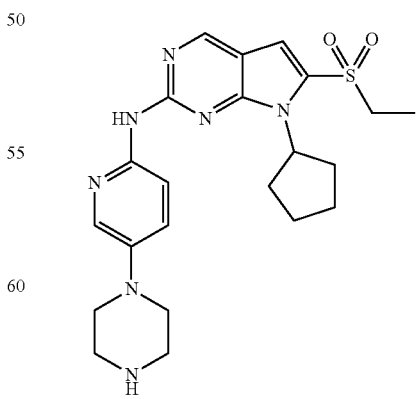

-continued

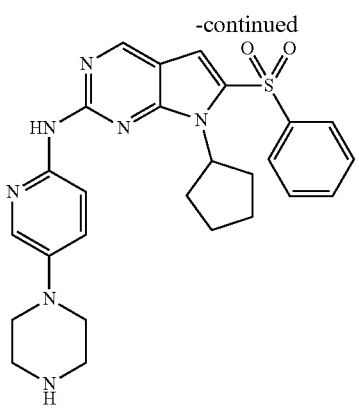

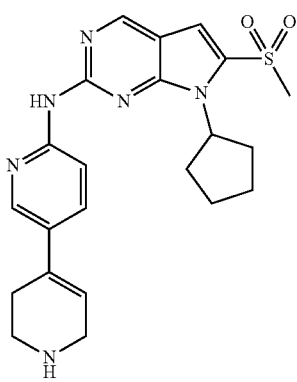

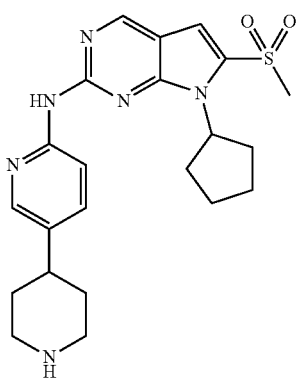

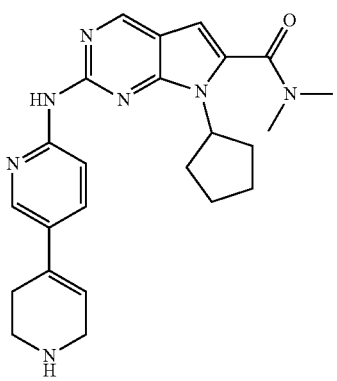

-continued

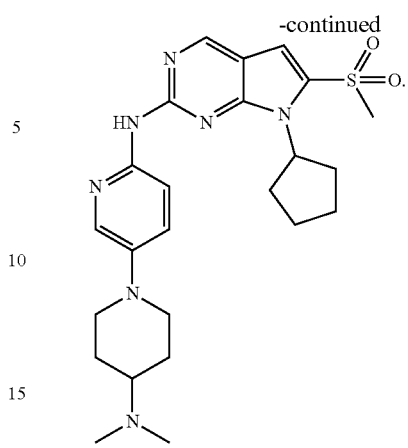

13. The compound or a pharmaceutically acceptable salt or solvate thereof according to claim 12, wherein the pharmaceutically acceptable salt is a hydrochloride salt.

14. A pharmaceutical composition, comprising the compound or a pharmaceutically acceptable salt or solvate thereof according to claim 1, and one or more pharmaceutically acceptable carriers or excipients.

15. A method for ameliorating, eliminating, inhibiting, and/or alleviating a disease associated with CDK4 and/or CDK6 inhibition, comprising administering to a subject in need thereof a therapeutically effective amount of the compound or a pharmaceutically acceptable salt or solvate thereof according to claim 1 wherein the disease associated with CDK4 and/or CDK6 inhibition is selected from the group consisting of breast cancer and colon cancer.

16. The compound or a pharmaceutically acceptable salt or solvate thereof according to claim 1, wherein the pharmaceutically acceptable salt is a hydrochloride salt.

17. The compound or a pharmaceutically acceptable salt or solvate thereof according to claim 4, wherein $R_5$ and $R_6$ are independently selected from methyl.

18. The compound or a pharmaceutically acceptable salt or solvate thereof according to claim 10, wherein the group

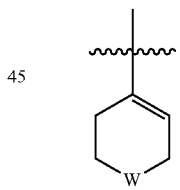

is

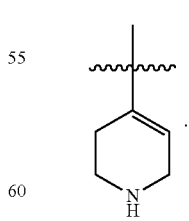

19. The compound or a pharmaceutically acceptable salt or solvate thereof according to claim 4, wherein $R_5$ and $R_6$ are independently selected from the group consisting of methyl and ethyl, which is optionally substituted by one or more $R_a$.

20. A compound of the formula
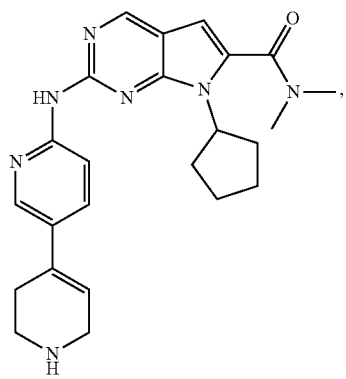 [SMILES: CN(C)C(=O)c1cc2cnc(Nc3ccc(C4=CCNCC4)cn3)nc2n1C1CCCC1]
or a pharmaceutically acceptable salt or solvate thereof.
* * * * *